(12) United States Patent
Ibrahim et al.

(10) Patent No.: US 10,497,552 B2
(45) Date of Patent: Dec. 3, 2019

(54) METHODS AND SYSTEMS FOR ION MANIPULATION

(71) Applicant: Battelle Memorial Institute, Richland, WA (US)

(72) Inventors: Yehia M. Ibrahim, Richland, WA (US); Aneesh Prabhakaran, Richland, WA (US); Sandilya V. B. Garimella, Richland, WA (US); Richard D. Smith, Richland, WA (US); Ailin Li, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/103,729

(22) Filed: Aug. 14, 2018

(65) Prior Publication Data

US 2019/0057852 A1 Feb. 21, 2019

Related U.S. Application Data

(60) Provisional application No. 62/546,419, filed on Aug. 16, 2017.

(51) Int. Cl.
*H01J 49/06* (2006.01)
*H01J 49/00* (2006.01)
*G01N 27/62* (2006.01)

(52) U.S. Cl.
CPC .......... *H01J 49/063* (2013.01); *G01N 27/622* (2013.01); *H01J 49/062* (2013.01)

(58) Field of Classification Search
CPC ...... H01J 49/062; H01J 49/065; H01J 49/063; H01J 49/022; H01J 49/4235;
(Continued)

(56) References Cited

U.S. PATENT DOCUMENTS 3,202,995 A * 8/1965 Schultz ................. H01Q 3/242
343/732
3,617,908 A * 11/1971 Greber .................... H05H 7/00
315/501

(Continued)

FOREIGN PATENT DOCUMENTS

AU 2014251354 B2 11/2017
AU 2016320584 A1 4/2018
(Continued)

OTHER PUBLICATIONS

Chen, et al., "Mobility-Selected Ion Trapping and Enrichment Using Structures for Lossless Ion Manipulations", Analytical Chemistry, Jan. 2016, 88, pp. 1728-1733.
(Continued)

*Primary Examiner* — David A Vanore
(74) *Attorney, Agent, or Firm* — Klarquist Sparkman, LLP

(57) ABSTRACT

An ion manipulation device comprises a plurality of electrode rings arranged longitudinally adjacent to each other and defining a central axis therethrough. At least one electrode ring comprises a plurality of electrodes arranged in a first planar pattern. Electrodes are configured to periodically receive a voltage to generate a circular traveling wave that rotates around the electrodes of each electrode ring to confine ions within an interior of the apparatus.

22 Claims, 28 Drawing Sheets

(58) Field of Classification Search
CPC ............... H01J 49/0095; H01J 49/427; H01J 2237/1215; H01J 37/16; H01J 49/403; H01J 49/4225; H01J 49/423; G01N 27/624
USPC ................ 250/281, 282, 292, 293, 396 R
See application file for complete search history.

(56) References Cited

U.S. PATENT DOCUMENTS

| | | | |
|---|---|---|---|
| 4,777,363 A | 10/1988 | Eiceman et al. | |
| 5,206,506 A | 4/1993 | Kirchner | |
| 5,572,035 A | 11/1996 | Franzen | |
| 5,834,771 A | 11/1998 | Yoon et al. | |
| 6,107,628 A | 8/2000 | Smith et al. | |
| 6,322,703 B1* | 11/2001 | Taniguchi | B01D 61/14 210/500.23 |
| 6,417,511 B1 | 7/2002 | Russ, IV | |
| 6,727,495 B2* | 4/2004 | Li | G01N 27/622 250/281 |
| 6,835,928 B2* | 12/2004 | Bateman | H01J 49/004 250/281 |
| 6,891,157 B2 | 5/2005 | Bateman et al. | |
| 6,960,760 B2 | 11/2005 | Bateman et al. | |
| 7,071,467 B2* | 7/2006 | Bateman | H01J 49/4225 250/292 |
| 7,095,013 B2 | 8/2006 | Bateman et al. | |
| 7,151,255 B2 | 12/2006 | Weiss et al. | |
| 7,157,698 B2 | 1/2007 | Makarov et al. | |
| 7,180,078 B2 | 2/2007 | Pau et al. | |
| 7,365,317 B2 | 4/2008 | Whitehouse et al. | |
| 7,391,021 B2 | 6/2008 | Stoermer et al. | |
| 7,405,401 B2 | 7/2008 | Hoyes | |
| 7,548,818 B2 | 6/2009 | Kieser | |
| 7,786,435 B2 | 8/2010 | Whitehouse et al. | |
| 7,838,826 B1 | 11/2010 | Park | |
| 7,872,228 B1 | 1/2011 | Kim et al. | |
| 7,888,635 B2 | 2/2011 | Belov et al. | |
| 7,928,375 B1 | 4/2011 | Mangan et al. | |
| 8,003,934 B2 | 8/2011 | Hieke | |
| 8,049,169 B2 | 11/2011 | Satake et al. | |
| 8,222,597 B2 | 7/2012 | Kim et al. | |
| 8,299,443 B1* | 10/2012 | Shvartsburg | H01J 49/066 250/292 |
| 8,319,180 B2 | 11/2012 | Nikolaev et al. | |
| 8,373,120 B2 | 2/2013 | Verentchikov | |
| 8,389,933 B2 | 3/2013 | Hoyes | |
| 8,410,429 B2 | 4/2013 | Franzen et al. | |
| 8,581,181 B2 | 11/2013 | Giles | |
| 8,658,969 B2* | 2/2014 | Nishiguchi | H01J 49/065 250/281 |
| 8,698,075 B2* | 4/2014 | Kurulugama | H01J 49/065 250/292 |
| 8,809,769 B2 | 8/2014 | Park | |
| 8,835,839 B1 | 9/2014 | Anderson et al. | |
| 8,841,608 B2* | 9/2014 | Shvartsburg | G01N 27/622 250/282 |
| 8,901,490 B1 | 12/2014 | Chen et al. | |
| 8,907,273 B1 | 12/2014 | Chen et al. | |
| 8,969,800 B1 | 3/2015 | Tolmachev et al. | |
| 9,165,693 B2* | 10/2015 | Urbanus | G21K 1/02 |
| 9,536,721 B2* | 1/2017 | Berdnikov | H01J 49/0095 |
| 9,704,701 B2* | 7/2017 | Ibrahim | H01J 49/26 |
| 9,812,311 B2 | 11/2017 | Anderson et al. | |
| 9,939,409 B2* | 4/2018 | Ibrahim | G01N 27/622 |
| 9,966,244 B2 | 5/2018 | Anderson et al. | |
| 10,139,366 B2* | 11/2018 | Atamanchuk | G01N 27/622 |
| 2001/0035498 A1 | 11/2001 | Li | |
| 2002/0074492 A1* | 6/2002 | Taniguchi | H01J 49/062 250/292 |
| 2003/0132379 A1 | 7/2003 | Li | |
| 2003/0222213 A1* | 12/2003 | Taniguchi | H01J 49/067 250/292 |
| 2004/0026611 A1 | 2/2004 | Bateman et al. | |
| 2004/0051038 A1* | 3/2004 | Taniguchi | H01J 49/065 250/288 |
| 2004/0089803 A1 | 5/2004 | Foley | |
| 2004/0222369 A1 | 11/2004 | Makarov et al. | |
| 2004/0251411 A1* | 12/2004 | Bateman | H01J 49/005 250/293 |
| 2005/0040327 A1 | 2/2005 | Lee et al. | |
| 2005/0109930 A1 | 5/2005 | Hill, Jr. et al. | |
| 2007/0034810 A1* | 2/2007 | Hoyes | H01J 49/427 250/396 R |
| 2007/0138384 A1 | 6/2007 | Keiser | |
| 2008/0073515 A1 | 3/2008 | Schoen | |
| 2009/0173880 A1 | 7/2009 | Bateman et al. | |
| 2009/0206250 A1 | 8/2009 | Wollnik | |
| 2011/0049357 A1 | 3/2011 | Giles | |
| 2011/0192969 A1 | 8/2011 | Verentchikov | |
| 2013/0175441 A1* | 7/2013 | Zanon | H01J 49/066 250/288 |
| 2013/0313421 A1* | 11/2013 | Taniguchi | H01J 49/063 250/281 |
| 2014/0061457 A1 | 3/2014 | Berdnikov et al. | |
| 2014/0124663 A1 | 5/2014 | Green et al. | |
| 2014/0145076 A1 | 5/2014 | Park | |
| 2014/0299766 A1 | 10/2014 | Anderson et al. | |
| 2014/0361163 A1* | 12/2014 | Taniguchi | H01J 49/063 250/287 |
| 2015/0028200 A1 | 1/2015 | Green et al. | |
| 2015/0364309 A1* | 12/2015 | Welkie | H01J 49/062 250/282 |
| 2015/0364313 A1* | 12/2015 | Zhang | H01J 49/065 250/288 |
| 2016/0027604 A1 | 1/2016 | Cho et al. | |
| 2016/0049287 A1 | 2/2016 | Ding et al. | |
| 2016/0071714 A1* | 3/2016 | Zhang | H01J 49/062 250/287 |
| 2016/0071715 A1* | 3/2016 | Anderson | H01J 49/062 315/111.81 |
| 2016/0189947 A1* | 6/2016 | Zhou | G01N 27/622 250/294 |
| 2016/0211129 A1* | 7/2016 | Gardner | H01J 49/4255 |
| 2017/0076931 A1 | 3/2017 | Ibrahim et al. | |
| 2017/0125229 A1 | 5/2017 | Giles et al. | |
| 2017/0200596 A1* | 7/2017 | Makarov | H01J 49/0422 |
| 2018/0061621 A1 | 3/2018 | Anderson et al. | |
| 2018/0068839 A1* | 3/2018 | Ibrahim | H01J 49/0095 |
| 2018/0254178 A1 | 9/2018 | Ibrahim et al. | |
| 2019/0004011 A1* | 1/2019 | Garimella | H01J 49/0027 |
| 2019/0057852 A1* | 2/2019 | Ibrahim | H01J 49/062 |
| 2019/0066993 A1* | 2/2019 | Ramsey | H01J 49/424 |
| 2019/0103261 A1* | 4/2019 | Ibrahim | H01J 49/061 |

FOREIGN PATENT DOCUMENTS

| | | |
|---|---|---|
| AU | 2016335524 A9 | 5/2018 |
| CA | 2908936 | 10/2014 |
| CA | 2997910 | 3/2017 |
| CA | 3000341 | 4/2017 |
| CN | 1361922 A | 7/2002 |
| CN | 101126738 A | 2/2008 |
| CN | 102163531 A | 8/2011 |
| CN | 102945786 A | 2/2013 |
| CN | 201680069722 | 8/2016 |
| CN | 105264637 B | 9/2017 |
| CN | 107507751 A | 12/2017 |
| CN | 108352288 A | 7/2018 |
| DE | 112013004733 | 6/2015 |
| EP | 1566828 A2 | 8/2005 |
| EP | 1825495 A2 | 8/2007 |
| EP | 2065917 A1 | 6/2009 |
| EP | 2913839 | 9/2015 |
| EP | 2984675 A1 | 2/2016 |
| EP | 3347913 A1 | 7/2018 |
| EP | 3359960 A1 | 8/2018 |
| GB | 2440970 A | 2/2008 |
| GB | 2506362 A | 4/2014 |
| JP | 2002-015699 | 1/2002 |
| JP | 2009532822 A | 9/2009 |
| JP | 2009535759 A | 10/2009 |

(56) References Cited

FOREIGN PATENT DOCUMENTS

| | | |
|---|---|---|
| JP | 2009537070 A | 10/2009 |
| JP | 2011529623 A | 12/2011 |
| JP | 2012503286 A | 2/2012 |
| JP | 2018-518405 | 5/2016 |
| JP | 2016514896 A | 5/2016 |
| JP | 2018528427 A | 9/2018 |
| SG | 11201801852 | 5/2016 |
| SG | 11201802494 | 8/2016 |
| SG | 11201508277 | 2/2018 |
| WO | WO 2006/064274 A2 | 6/2006 |
| WO | WO 2007/133469 A2 | 11/2007 |
| WO | WO 2010/014077 A1 | 2/2010 |
| WO | WO 2010/032015 A1 | 3/2010 |
| WO | WO 2011/089419 A2 | 7/2011 |
| WO | WO 2012/116765 A1 | 9/2012 |
| WO | WO 2013/018529 A1 | 2/2013 |
| WO | WO 2014/048837 A2 | 4/2014 |
| WO | WO 2014/168660 A1 | 10/2014 |
| WO | WO 2015/056872 | 4/2015 |
| WO | WO 2015/097462 | 7/2015 |
| WO | WO 2016/069104 A1 | 5/2016 |
| WO | WO 2017/044159 | 3/2017 |
| WO | WO 2017/062102 | 4/2017 |

OTHER PUBLICATIONS

English translation of the first Chinese office action from corresponding Chinese patent application No. 201480032436.7, dated Oct. 14, 2016, 5 pages.

English translation of the search report from corresponding Chinese patent application No. 201480032436.7, dated Sep. 29, 2016, 2 pages.

Deng et al., "Serpentine Ultralong Path with Extended Routing (SUPER) High Resolution Traveling Wave Ion Mobility-MS using Structures for Lossles Ion Manipulations", Analytical Chemistry, Mar. 2017, 89, pp. 4628-4634.

European Search Report for European Patent Application No. 14782685.3, dated Oct. 25, 2016.

Examination Report No. 1 for related Australian Application No. 2016320584, dated Jun. 27, 2018, 3 pages.

Examination Report No. 2 for related Australian Application No. 2016320584, dated Sep. 3, 2018, 2 pages.

Examination Report No. 1 for related Australian Application No. 2016335524, dated May 15, 2018, 4 pages.

First Office Action for related Canadian Application No. 2,997,910, dated May 4, 2018, 4 pages.

First Office Action for related Canadian Application No. 3,000,341, dated Jul. 30, 2018, 5 pages.

First Office Action for Chinese Application No. 201680065673.2, dated Sep. 30, 2018, 14 pages.

First Office Action for related Japanese Application No. 2018-513012, dated Aug. 2, 2018, 2 pages; with English translation, 2 pages.

Hamid, Ahmed M. et al., "Characterization of Travelling Wave Ion Mobility Separations in Structures for Lossless Ion Manipulations," Analytical Chemistry, 87(22):11301-11308 (Nov. 2015).

International Search Report and Written Opinion for PCT/US2016/047070 (dated Nov. 7, 2016).

International Search Report and Written Opinion issued in related International Application No. PCT/US2016/030455, dated Jul. 25, 2016, 19 pages.

International Search Report and Written Opinion for related International Application No. PCT/US2014/011291, dated Jun. 6, 2014, 2 pages.

International Search Report and Written Opinion for related International Application No. PCT/US2018/041607, dated Sep. 20, 2018, 18 pp.

International Search Report and Written Opinion for related International Application No. PCT/US2018/046752, dated Dec. 4, 2018, 12 pp.

Search Report from corresponding Singapore patent application No. 11201508277X, dated Mar. 6, 2016, 7 pages.

Tolmachev, et al., "Characterization of Ion Dynamics in Structures for Lossless Ion Manipulations," Analytical Chemistry, 86(18):9162-9168 (Sep. 2014).

Webb et al., "Mobility-Resolved Ion Selection in Uniform Drift Field Ion Mobility Spectrometry/Mass Spectrometry: Dynamic Switching in Structures for Lossless Ion Manipulations," Analytical Chemistry, Oct. 2014, 86, 9632-9637.

Wojcik et al., "Lipid and Glycolipid Isomer Analyses Using Uitra-High Resolution Ion Mobility Spectrometry Separations", International Jouranl of Molecular Sciences, Jan. 2017, 18, 12 pp.

Written Opinion from the Intellectual Property Office of Singapore for related Application No. 11201802494Q, dated Aug. 21, 2018, 8 pages.

Written Opinion from the Intellectual Property Office of Singapore for related Application No. 11201801852Q, dated Nov. 22, 2018, 26 pages.

English translation of the first Chinese office action from corresponding Chinese patent application No. 201710799275.X, dated Nov. 2, 2018, 12 pages.

\* cited by examiner

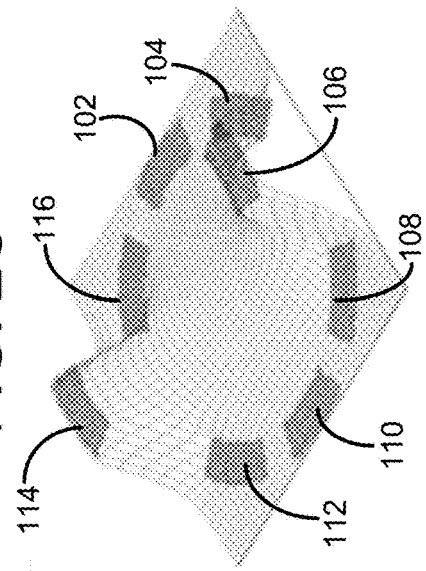
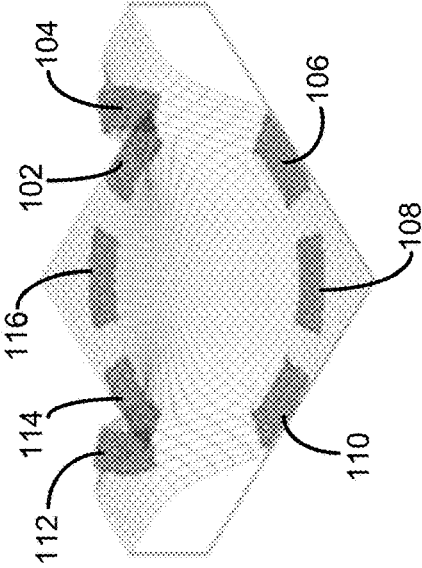
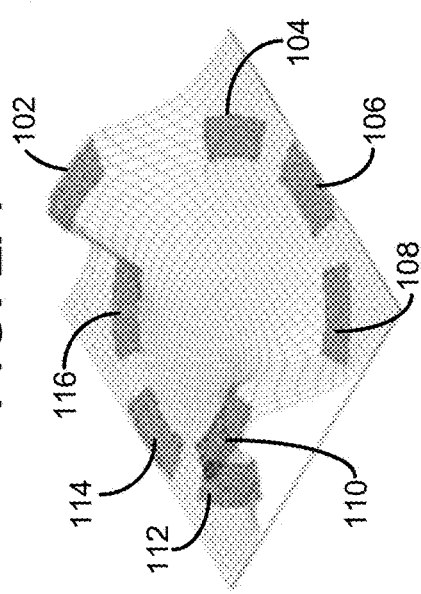

760 Torr
(16 electrode arrangement)
TW: 300V, 40kHz

50 Torr
TW: 180V, 180kHz

760 Torr
TW: 450V, 40kHz

100 Torr
TW: 150V, 100kHz

760 Torr
(8 electrode arrangement)
TW: 450V, 40kHz

1400 Torr
TW: 450V, 40kHz

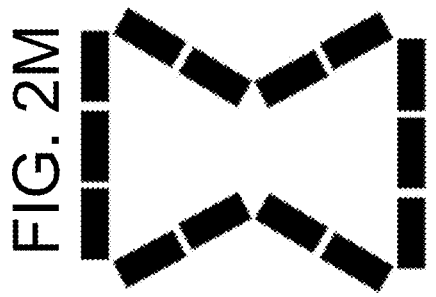
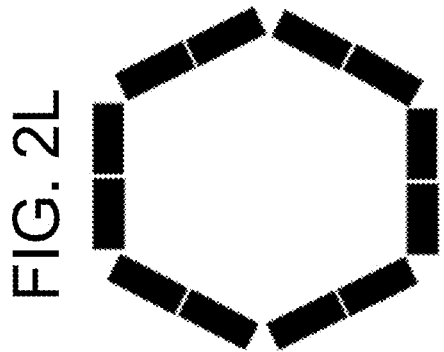
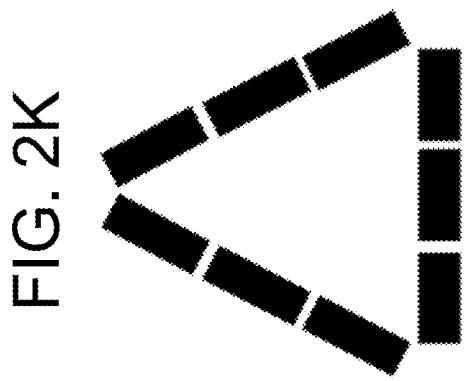
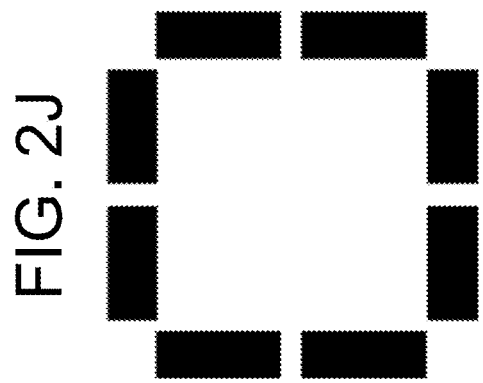

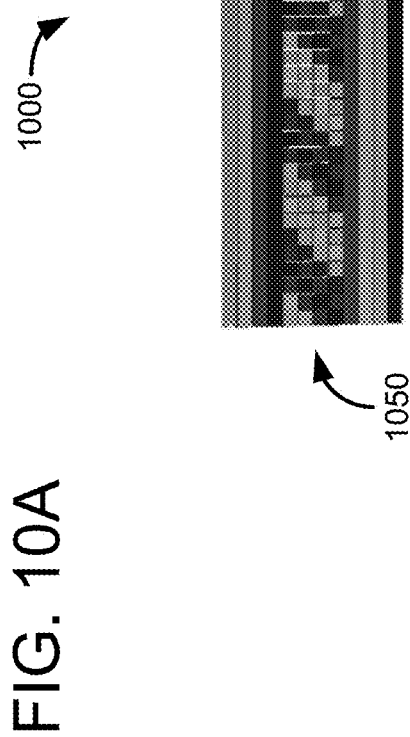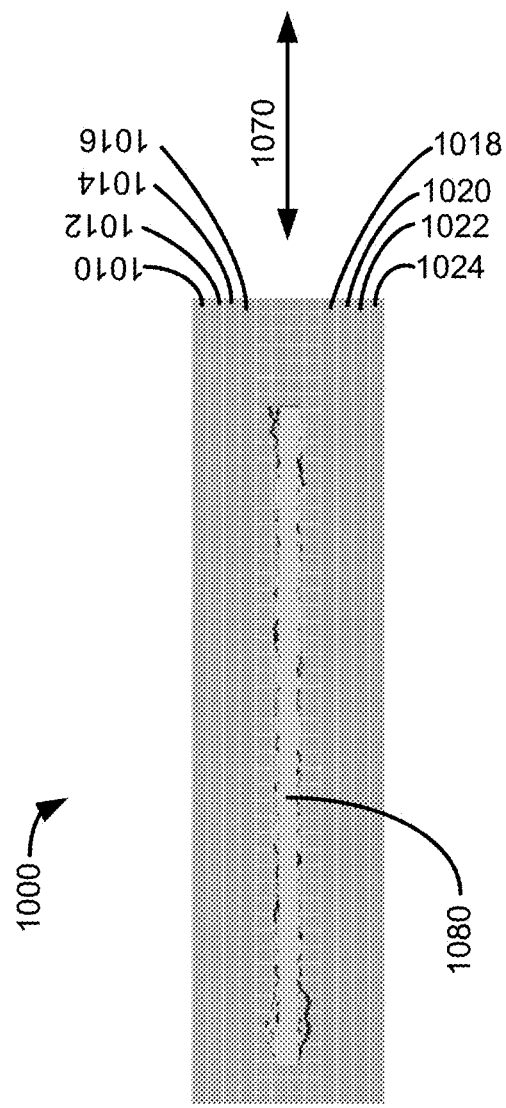

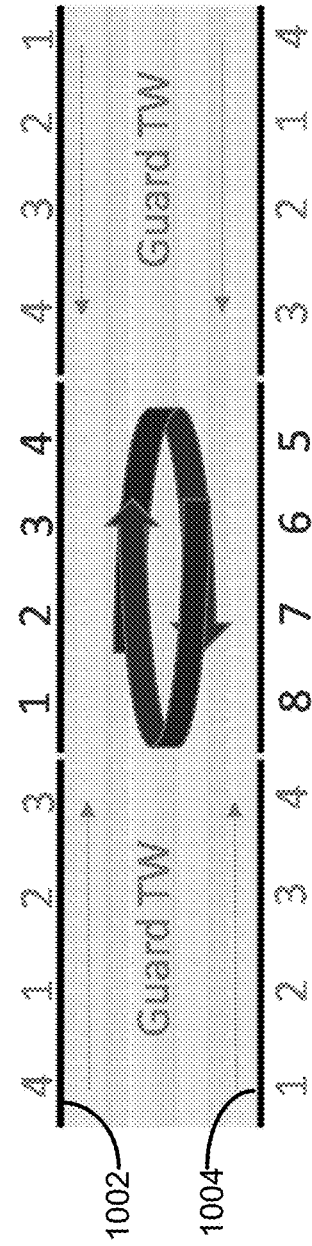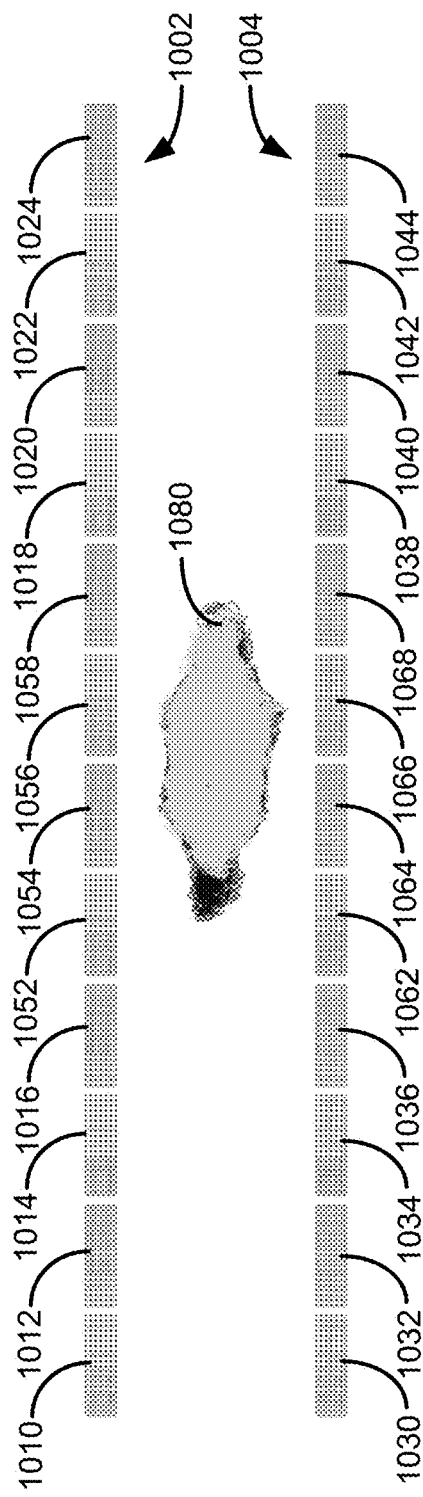
FIG. 10C
FIG. 10D

METHODS AND SYSTEMS FOR ION MANIPULATION

CROSS REFERENCE TO RELATED APPLICATION

This application claims the benefit of U.S. Provisional Application Ser. No. 62/546,419, entitled "METHODS AND DEVICE FOR ION CONFINEMENT AND MANIPULATION AT OR BELOW ATMOSPHERIC PRESSURE", filed on Aug. 16, 2017, which is incorporated in its entirety by reference herein.

ACKNOWLEDGMENT OF GOVERNMENT SUPPORT

This disclosure was made with Government support under Contract DE-AC05-76RL01830 awarded by the U.S. Department of Energy. The Government has certain rights in the invention.

TECHNICAL FIELD

This invention relates to ion manipulation. More specifically, this invention relates to the use of traveling waves to trap ions or to confine ions or to manipulate ions, or to separate ions, or any combination thereof, on the basis of difference in their mobilities, over a wide range of pressures, including at or near atmospheric pressure.

BACKGROUND

Trapping and manipulating ions is widely used in analytical techniques such as mass spectrometry (MS). Ion traps are also used for other applications such as quantum computing. Trapped ions can be used for accumulating a population of ions to be injected into an ion mobility drift cell to perform ion mobility spectrometry (IMS) to separate, identify, or distinguish ions or charged particles. IMS can be employed in a variety of applications such as separating structural isomers and resolving conformational features of charged chemical compounds, macromolecules, and essentially any charged particles. IMS may also be employed to augment mass spectroscopy in a broad range of applications, including metabolomics, glycomics, and proteomics, as well as for a broad range of applications involving essentially any compound that can be effectively ionized.

For example, when performing IMS in a conventional drift tube, a sample composed of ions having different mobilities can be injected into a first end of an enclosed cell containing a carrier gas, also referred to as a buffer gas. In the cell, the ions can move from the first end of the cell to a second end of the cell under the influence of one or more applied electric fields. The ions can be subsequently detected at the second end of the cell as a function of time. The sample ions can achieve a maximum, constant velocity (i.e., a terminal velocity) arising from the net effects of acceleration due to the applied electric fields and deceleration due to collisions with the buffer gas molecules. The terminal velocity of the ions increases with the magnitude of the electric field and is proportional to their respective mobilities, which are related to ion characteristics such as mass, size, shape, and charge. Ions that differ in one or more of these characteristics will exhibit different mobilities when moving through a given buffer gas under a given electric field and, therefore, will achieve different terminal velocities. As a result, each ion exhibits a characteristic time for travel from the first end of the cell to the second end of the cell. By measuring this characteristic travel time for ions within a sample, the ions can be distinguished or identified.

There are a number of IMS formats used for chemical and biochemical analysis, including constant field drift tube ion mobility spectrometry (DT-IMS), high field asymmetric ion mobility spectrometry (FA-IMS), differential mobility analysis (DMA), trapped ion mobility spectrometry (TIMS), and traveling wave ion mobility spectrometry (TW-IMS). These formats vary in the manner by which the electric field is applied to separate the ions within the IMS cell or device. However, in addition to separating ions, IMS devices ideally also confine ions within the device as the ions move through the device to prevent the ions from colliding with the surfaces of the device itself and causing loss of ions.

Ion traps, on the other hand, manipulate ions based on their mass to charge ratio. Ions react to electric field oscillation in radio frequency (RF) by executing a simple harmonic motion between electrodes on which the RF fields are applied. In this way, they remain in dynamic equilibrium and can be effectively trapped, manipulated, and interacted with by other ions, neutrals, photons, etc. This kind of ion confinement or ion trapping is possible at vacuum conditions (e.g., pressure less than 0.1 Torr). Using design variants, like stacked ring ion guides with opposite polarity of RF on adjacent electrodes, the pressure up to which ions can be trapped or confined within a volume can be increased to 50 Torr in devices such as ion funnels and ion funnel traps. However, ion trapping at much higher pressures is not possible using RF fields as the collisions of ions with background neutrals prevents them from executing simple harmonic motion critical to ion confinement.

For similar reasons as discussed above, conventional IMS devices can only efficiently confine ions at low pressures, typically no more than about 10 Torr in most devices or potentially up to about 50 Torr in some designs. As such, many conventional IMS devices are designed for operation in low pressure or near vacuum conditions using well understood methods involving pseudopotentials generated using RF electric fields. The combination of low pressure operation (e.g., the use of a confining chamber and an associated pumping system) and an RF power supply needed to create ion confinement fields greatly increases the size, weight, and cost of operating such devices and limits the applications for which they can be used. Additionally, the low pressure operation of IMS devices for confinement can lead to loss of ions during transport from an atmospheric pressure ion source to the vacuum stage in which the IMS device operates. Also, other applications could be greatly simplified by the ability to trap ions within a volume at higher pressures than is currently possible. Specifically, it would be highly advantageous to be able to confine and manipulate ions at atmospheric pressure.

Accordingly, there is a need for ion manipulation devices that can operate effectively at atmospheric pressure and more generally at all pressures (or at conditions with a low ratio of electric field strength to ion density, which depends on pressure).

SUMMARY

In general, embodiments of the disclosure provide systems and corresponding methods for trapping ions or confining ions or manipulating ions, or separating ions, or any combination thereof, at atmospheric pressure. The embodiments also provide systems and methods that can trap ions or confine ions or manipulate ions, or separate ions, or any combination thereof, above atmospheric pressure. The embodiments also provide systems and methods for trapping ions or confining ions or manipulating ions, or separating ions, or any combination thereof, below atmospheric pressure but above a pressure of 0.1 Torr. The embodiments also provide systems and methods for losslessly manipulating ions at any pressure above approximately 0.1 Torr. The embodiments disclosed herein generally involve the use of a revolving voltage profile (e.g., a cyclic traveling wave) to maintain ion trajectories in an equilibrium within the volume encompassed by the electrodes that define the revolving voltage profile.

In one representative embodiment, an apparatus can comprise a plurality of electrode rings arranged longitudinally adjacent to each other and defining a central axis therethrough. Each electrode ring can constitute an arrangement of cyclically arranged electrodes. Each electrode ring can comprise a plurality of electrodes arranged in a first planar pattern. Each electrode can be configured to periodically receive a voltage to generate a "circular" traveling wave; that is a traveling wave that rotates the potentials applied around the electrodes of each electrode ring to confine ions within an interior of the apparatus.

In any of the disclosed embodiments, the first pattern can have rotational symmetry. In any of the disclosed embodiments, the first planar pattern can define an enclosed volume. In any of the disclosed embodiments, the first planar pattern can be a circular arrangement of electrodes. In any of the disclosed embodiments, the first planar pattern can be a rectangular arrangement of electrodes. In any of the disclosed embodiments, the first planar pattern can be a triangular, pentagonal, hexagonal, octagonal, or any complex cyclical arrangement of electrodes with any arbitrary number of electrodes making up the arrangement of electrodes.

In any of the disclosed embodiments, there can be a gap between each pair of axially adjacent electrode rings. In any of the disclosed embodiments, the gap can be sized such that the electrodes of each electrode ring are electrically isolated from the electrodes of axially adjacent electrode rings. In any of the disclosed embodiments, there can be a dielectric material positioned between each pair of axially adjacent electrode rings, or another set of electrodes.

In any of the disclosed embodiments, an arbitrary number of electrode rings can be stacked adjacent to each other to create an ion trap of arbitrary length.

In any of the disclosed embodiments, the stacked electrode rings may be in electrical contact such that individual electrodes that comprise an electrode ring are in contact with corresponding electrodes of an adjacent electrode ring.

In any of the disclosed embodiments, the electrode rings may be isolated from adjacent electrode rings by introducing a dielectric material of arbitrary thickness between the electrode rings.

In any of the disclosed embodiments, the electrode rings can be stacked in such a way that any electrode of an electrode ring may be in electrical contact with any other electrode of an adjacent electrode ring such that a revolving traveling wave on one electrode ring can be phase shifted with respect to the revolving traveling wave on an adjacent electrode ring by any chosen value (e.g., $2\pi i/n_e$ where "i" is the electrode number 1 to $n_e$ and $n_e$ is the number of electrodes in a ring).

In any of the disclosed embodiments, the circular traveling wave on each electrode ring can be out of phase with the circular traveling wave on each adjacent electrode ring. In any of the disclosed embodiments, there can be a gap between each radially adjacent electrode of each electrode ring.

In any of the disclosed embodiments, the apparatus may be configured to function as an ion trap to confine ions in the gas phase at all pressure above 0.1 Torr. A trap created using any of the disclosed embodiments may be coupled with any source to introduce specific neutral gas molecules to perform ion/neutral reactions at all pressures above 0.1 Torr. A trap created using any of the disclosed embodiments may be coupled with any ion source to introduce ions into the ion trap device at all pressure above 0.1 Torr. The disclosed devices may be referred to as an "All Pressure Ion Confinement" or APIC devices and the methods to do so as described herein may be referred to as APIC methods. The APIC devices and methods may be used with any ambient, atmospheric pressure, or sub-ambient pressure ion sources to introduce ions of both polarities (either separately or simultaneously) into an APIC device and manipulate (through indefinite confinement, separation, ion/ion reaction, ion/neutral reaction and/or ion/photon reaction) the same using any plurality of voltage applications as enabled by the embodiments described above.

In any of the disclosed embodiments, each electrode ring can be configured to receive a superimposed DC voltage to create a DC voltage gradient along a length of the apparatus to guide ions trapped inside the device along the central axis. In any of the disclosed embodiments, each electrode ring can be configured to receive a superimposed transient DC voltage to create an axial traveling wave to guide ions along the central axis. The applied DC voltage can be used to enable ion separation based on IMS.

In any of the disclosed embodiments, the apparatus can further comprise a second plurality of segmented electrodes radially interleaved between the electrodes of each electrode ring.

In any of the disclosed embodiments, the second plurality of segmented electrodes can be configured to receive a DC voltage to create a DC voltage gradient along a length of the apparatus to guide ions along the central axis.

In any of the disclosed embodiments, the second plurality of segmented electrodes can be configured to receive a superimposed transient DC voltage to create an axial traveling wave to guide ions along the central axis.

In any of the disclosed embodiments, the electrode rings can form a substantially T-shaped configuration, allowing ions to be switched to either of two paths at the junction of the T-shaped configuration.

In any of the disclosed embodiments, the apparatus can further comprise a plurality of unsegmented electrodes axially interleaved between each of the electrode rings. In any of the disclosed embodiments, the unsegmented electrodes can be configured to receive a DC voltage to create an axial DC voltage gradient along the unsegmented electrode to guide the ions along the central axis. In any of the disclosed embodiments, the unsegmented electrodes can be configured to receive a transient DC voltage to create an axial traveling wave to guide ions along the central axis.

In any of the disclosed embodiments, a cyclical revolving traveling wave can be created by using two parallel surfaces comprising a plurality of electrodes on each surface.

In another representative embodiment, an apparatus can comprise a first surface and a second surface positioned parallel to and spaced apart from each other and defining a central axis therebetween, outer arrays of electrodes coupled to each of the first and second surface, and an inner array of electrode rows positioned between the outer arrays of electrodes. Each electrode row can comprise a plurality of adjacent electrodes. The electrodes of each electrode row can be configured to periodically receive a voltage to generate a circular traveling wave that rotates around the electrodes of each electrode row on the first surface and a corresponding electrode row on the second surface to confine ions between the first surface and the second surface, with the outer electrode surface providing voltages that prevent the confined ions from laterally escaping between the two parallel inner surfaces.

In any of the disclosed embodiments, the outer arrays of electrodes and the inner array of electrode rows can extend substantially along the length of the first and second surface.

In any of the disclosed embodiments, the outer arrays of electrodes can comprise a first outer array of electrodes and a second outer array of electrodes. The first outer array of electrodes can positioned on one side of the inner array of electrode rows and the second outer array of electrodes can be positioned on the other side of the inner array of electrode rows.

In any of the disclosed embodiments, the outer arrays of electrodes can be configured to periodically receive a DC voltage to create a traveling wave electric field that confines ions between the outer arrays of electrodes.

In any of the disclosed embodiments, the outer arrays of electrodes can be configured to receive a DC voltage such that ions are confined between the outer arrays of electrodes.

In any of the disclosed embodiments, each of the electrode rows can be configured to receive a superimposed DC voltage to create a DC voltage gradient along a length of the apparatus such that ions are guided along the central axis.

In any of the disclosed embodiments, the electrodes of the inner array of electrode rows can be configured to receive a superimposed transient DC voltage to create an axial traveling wave to guide ions along the central axis.

In any of the disclosed embodiments, the apparatus can further comprise a plurality of unsegmented electrodes axially interleaved between each electrode row.

In any of the disclosed embodiments, the unsegmented electrodes can be configured to receive a DC voltage to create a DC voltage gradient along the unsegmented electrodes to guide ions along the central axis.

In any of the disclosed embodiments, the unsegmented electrodes can be configured to receive a transient DC voltage to create an axial traveling wave to guide ions along the central axis.

In any of the disclosed embodiments, the first and second surface can each be arranged in a substantially L-shaped configuration comprising a first portion oriented in a first direction, a second portion oriented in a second direction substantially parallel to the first portion, and a corner portion positioned at the junction between the first portion and the second portion.

In any of the disclosed embodiments, the first and second surface of the corner portion can each comprise a plurality of unsegmented electrodes arranged at various angles with respect to the first portion and the second portion such that ions are guided from the first portion to the second portion.

In another representative embodiment, a method of manipulating ions can comprise injecting ions within an interior of an apparatus comprising a plurality of electrode rings arranged longitudinally adjacent to each other and defining a central axis therethrough, wherein each electrode ring comprises a plurality of electrodes arranged in a first planar pattern, and applying a periodic voltage to each electrode of each electrode ring to generate a circular traveling wave that rotates around the electrodes of each electrode ring to confine ions within the interior of the apparatus.

In any of the disclosed embodiments, the method can further comprise applying a superimposed DC voltage to each electrode ring to create a DC voltage gradient along a length of the apparatus to guide ions along the central axis.

In any of the disclosed embodiments, the method can further comprise applying a superimposed transient DC voltage to the electrode rings to create an axial traveling wave to guide ions along the central axis.

In another representative embodiment, a method of manipulating ions can comprise injecting ions between a first surface and a second surface positioned parallel to and spaced apart from each other and defining a central axis therebetween, wherein the first surface and the second surface each comprise outer arrays of electrodes and an inner array of electrode rows positioned between the outer arrays of electrodes, each electrode comprising a plurality of adjacent electrodes, and applying a periodic voltage to each electrode of each electrode row to generate a circular traveling wave that rotates around the electrodes of each electrode row on the first surface and a corresponding electrode row on the second surface to confine ions between the first surface and the second surface.

In any of the disclosed embodiments, the method can further comprise applying a period DC voltage to the outer arrays of electrodes to create a traveling wave electric field that confines ions between the outer arrays of electrodes.

In any of the disclosed embodiments, the method can further comprise applying a DC voltage to the outer arrays of electrodes such that ions are confined between the outer arrays of electrodes.

In any of the disclosed embodiments, the method can further comprise applying a superimposed DC voltage to the electrode rows to create a DC voltage gradient along a length of the apparatus such that ions are guided along the central axis.

In any of the disclosed embodiments, the method can further comprise applying a superimposed transient DC voltage to the electrodes of the inner array of electrode rows to create an axial traveling wave to guide ions along the central axis.

The foregoing and other objects, features, and advantages of the disclosed technology will become more apparent from the following detailed description, which proceeds with reference to the accompanying figures.

BRIEF DESCRIPTION OF THE DRAWINGS

These and other features will be more readily understood from the following detailed description taken in conjunction with the accompanying drawings, in which:

FIGS. 2A-2C are schematic representations of voltages applied to electrodes of the exemplary ion manipulation device of FIGS. 1A-1B.

FIGS. 2J-2M show schematic representations of other exemplary electrode arrangements for use with disclosed ion manipulation devices.

FIGS. 10A-10D are schematic representations illustrating another exemplary embodiment of the disclosed ion manipulation devices.

DETAILED DESCRIPTION

Figure 1B:
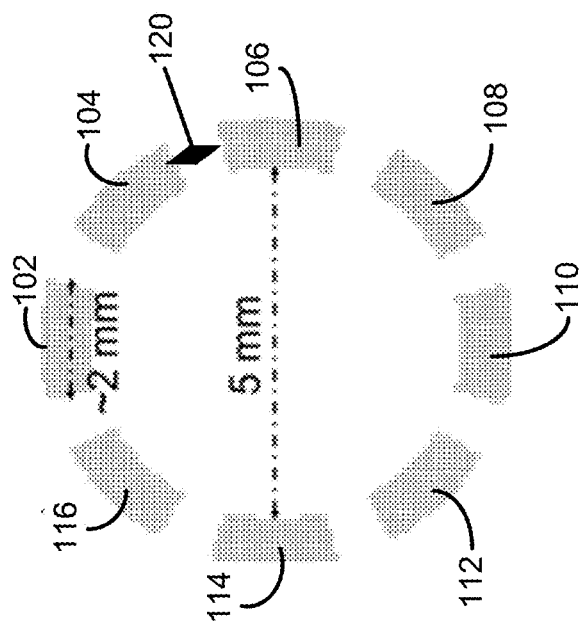
FIGS. 1A-1B are schematic representations illustrating an exemplary embodiment of the disclosed ion manipulation devices.

Certain exemplary embodiments will now be described to provide an overall understanding of the principles of the structure, function, manufacture, and use of the systems, devices, and methods disclosed herein.

The disclosure of numerical ranges should be understood as referring to each discrete point within the range, inclusive of endpoints, unless otherwise noted. Unless otherwise indicated, all numbers expressing quantities of components, dimensions, properties, percentages, and so forth, as used in the specification or claims are to be understood as being modified by the term "about." Accordingly, unless otherwise implicitly or explicitly indicated, or unless the context if properly understood by a person of ordinary skill in the art to have a more definitive construction, non-numerical properties or characteristics or the like, such traveling waves and so forth, as used in the specification or claims are to be understood as being modified by the term "substantially," meaning to a great extent or degree as would be understood by those skilled in the technical field. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. Accordingly, unless otherwise indicated, implicitly or explicitly, the numerical parameters and/or non-numerical properties or characteristics or the like, set forth are approximations that may depend on the desired properties sought, limits of detection under standard test conditions/methods, limitations of the processing method, the understood meanings of the terms in the technical field, and/or the nature of the parameter or property. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

The present invention is directed to devices, apparatuses, and methods of effectively trapping, or confining, or manipulating, or any combination thereof, ions at pressures including atmospheric pressure, above atmospheric pressure or below atmospheric pressure but above 0.1 Torr. Ion traps generally use high E/N (ratio of electric field to neutral particle density) conditions and RF voltages to perform trapping, analysis, and a host of other functions. Known ion traps cannot trap ions at low E/N conditions. The embodiments disclosed herein allow for trapping of ions at low E/N conditions by using rotating traveling waves (RTW) that move between adjacent electrodes at kHz frequencies. The ions are maintained away from neutralizing surfaces by using the forward or backward motion that occurs due to the RTW. This motion of ions under these low E/N conditions means that ions move based on their ionic mobilities. The ions which move faster than the frequency of RTW get neutralized, whereas those ions which move slower than the RTW frequency execute a backward and forward motion within the volume encompassed by the electrodes applied with RTW voltages. Such ions remain confined within the volume and the device functions as a high pressure or low E/N ion mobility based ion trap. Certain embodiments of the present invention use electric fields to create field-defined pathways, traps, and switches to manipulate these trapped ions in the gas phase, and do so at higher pressures. Such manipulations are not possible with current ion traps as they are not effective beyond a maximum pressure of about 50 Torr. Where, the disclosed embodiments allow such confinement and manipulation at all pressure above about 0.1 Torr. Some embodiments disclosed herein are ion manipulation devices that can perform manipulation of ions including, but not limited to, controlling ion paths, separating ions, reacting ions, and trapping and/or accumulating ions. Embodiments of the ion manipulation devices can enable complex sequences of ion separations, transfers, path switching, and trapping to occur in the space between various electrode arrangements.

Manipulation of ions is an important aspect of IMS devices. Ideally, such devices are able to transport charged particles (e.g., ions) from one location to another with low loss and are also able to separate the charged particles based on their mobility. In addition, it can be desirable for an IMS device to store and/or react to ions. It is not possible for a static configuration of electric fields to trap or confine ions. Accordingly, IMS devices typically confine ions using electric fields that change over time. For example, a pseudopotential field can be created by applying an RF voltage to various electrodes out of phase with each other. If operated at a high enough frequency, the generated pseudopotential will confine ions within a certain region. However, as pressure increases, the ability to confine ions using pseudopotentials generated by RF voltages decreases. At increasing pressures (e.g., decreasing E/N due to increasing natural gas density N), other forces such as thermal energy overcome the pseudopotential as the RF levels needed for confinement become impractical. RF pseudopotentials fail to confine ions above a pressure of about 50 Torr in known devices. Therefore, at higher pressures above 50 Torr, and specifically at atmospheric pressure or above, pseudopotentials generated by RF voltages are not able to confine ions without ion loss. As such, these types of devices can only be operated at pressures well below atmospheric pressure (typically less than $1/100^{th}$ of atmospheric pressure). Atmospheric pressure is understood to have its plain and ordinary meaning as understood by those of ordinary skill in the relevant art, typically understood to mean the pressure exerted by the weight of the atmosphere, which at sea level has a mean value of 101,325 Pascals or 760 Torr.

In embodiments of the present invention, rather than applying RF voltages to electrodes to confine ions, embodiments of IMS and related devices are disclosed that include a plurality of electrodes arranged in particular planar patterns around the exterior of a device. A DC voltage can then be applied sequentially to each such electrode. When a DC voltage is applied to a particular electrode, ions are directed away from that electrode by the electric field created by the applied voltage and ions are directed toward an adjacent electrode with a ground voltage. The ions move away from the high voltage electrode and towards the grounded electrode at a speed proportional to the ion mobility and electric field strength (since the pressure is higher than 0.1 Torr such that the general E/N is low and ion acceleration is damped by background neutral collisions). At a slightly later time interval, a voltage is applied to the next electrode (which was at a ground voltage during the earlier time interval) repelling the ions now from this electrode and moving them towards the next adjacent electrode. The ion trajectory will stably be confined away from these electrode when voltages are continually applied in this manner to each electrode of an electrode array comprising a cyclical arrangement of electrodes. This creates a traveling wave as the applied voltage rotates cyclically around the electrodes. If this traveling wave has an optimal frequency, ions will continually move away from the applied voltage and will be confined to a region within the area enclosed by the electrode pattern. The optimal frequency is determined by the speed of the ions moving from the high electrode voltage to the grounded electrode. If the ion speed is high, such that by the time the voltage is applied to the next electrode, the ion will reach this electrode and be neutralized by hitting the electrode surface. However, if ions are slow enough (or equivalently the rate at which the voltage moves is fast enough), then ions are continually pushed away from the electrode surface. The optimal frequency depends primarily on the size of the charged particles (e.g., a mass-to-charge ratio or ion mobility) and the gas/fluid density (e.g., pressure). Because this traveling wave results from the application of DC voltages or AC waveforms that create traveling waves of similar amplitudes and velocities, ion confinement can be provided at pressures where conventional RF confinement approaches fail. As such, devices disclosed herein can operate at approximately pressures above 0.1 Torr up to atmospheric pressure and above. Operation at much higher pressures, or in dense gases or liquids can be facilitated by the use of lower traveling wave velocities and higher amplitudes.

Typically, the lowest pressure at which certain of the disclosed devices can operate is that pressure which for the given device dimensions at applied voltages provides low E/N conditions (e.g., E/N less than 50 Townsends). This corresponds to pressure of 0.8 Torr in typical preferred embodiments. By subtle variations in design, the low E/N can be obtained up to a low pressure of 0.1 Torr. Below approximately 0.1 Torr, the E/N is generally high and ions accelerate with applied fields and can no longer be confined with the methods described herein and one must revert back to oscillating RF fields to confine ions. There is essentially no upper pressure limit for confining ions using the methods described herein. In addition to a traveling wave that confines ions radially, other voltages can be superimposed on the electrodes to guide ions axially through the device and to separate ions based on their mobility.

Figure 1A:
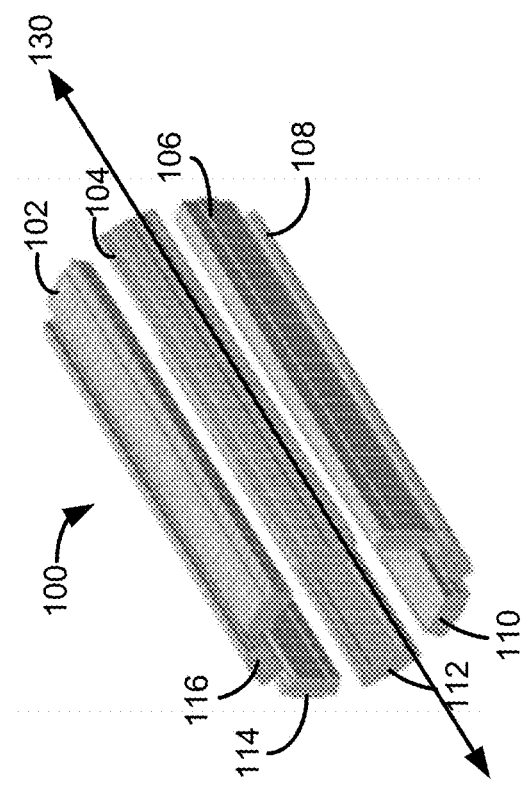

The methods and devices disclosed herein involve various arrangements of electrodes for confining and manipulating ions. FIGS. 1A and 1B show one embodiment of an ion manipulation device 100.

FIG. 1A shows a perspective view of an ion manipulation device 100. FIG. 1B shows a cross-sectional view of the device 100. The ion manipulation device 100 includes elongated electrodes 102, 104, 106, 108, 110, 112, 114, 116 arranged cyclically about an axis creating an internal volume within which ions are intended to be trapped. These electrodes are arranged in a circular pattern with rotational symmetry. The arrangement of the electrodes of the device 100 defines a central axis 130 and the electrodes are elongated in a direction parallel to the central axis. The arrangement of the electrodes defines an enclosed volume in which to contain ions. In the illustrated example, the device 100 has eight electrodes. However, in other embodiments, the device can have more than eight electrodes or less than eight electrodes so long as the electrodes form a roughly circular or enclosing pattern around the central axis. The device 100 must have at least three elongated electrodes so that an applied voltage can alternate between the three electrodes as explained below.

In the illustrated embodiment, as shown in FIG. 1B, the inner diameter of the device 100 (i.e., the distance between two opposite electrodes) is 5 mm and the width of each electrode is 2 mm. However, in other embodiments, the inner diameter of the device can be between 2 mm and 10 mm and the width between 0.5 mm and 5 mm. In certain other embodiments, inner diameter can be between 4 mm and 8 mm and the width of the electrodes can be between 1.5 mm and 2 mm.

In the illustrated example, there can be a gap 120 between each electrode. In some examples, the gaps 120 can comprise empty space or a non-conductive surface. In some examples, the gaps 120 can be filled with dielectric material. In some examples, the gaps 120 can be filled with other electrodes, as explained in further detail below. The gap 120 can provide a separation between the electrodes such that a voltage can be separately applied to each electrode. In operation, ions can be guided through the interior of the device 100 along the central axis 130 and voltages can be applied to the electrodes to confine the ions within the interior of the device 100, as disclosed herein.

In the illustrated example, a voltage source (not shown) can be coupled to the device 100 and the voltage source can apply a voltage to each of the electrodes. When a transient voltage is applied to an electrode, the applied potential creates an electrical field that repels ions and directs ions away from the electrode and towards the central axis 130. In the illustrated example, a voltage is applied to the electrodes in a rotating pattern to confine ions within the device 100, as disclosed herein.

FIGS. 2A, 2B, and 2C illustrate the voltage applied to the electrodes 102, 104, 106, 108, 110, 112, 114, 116 over time. In the illustrated embodiment of FIGS. 2A-2C, the elevation map shows the potential of each electrode during a certain time interval. For example, in FIG. 2A, a voltage is applied to electrodes 102 and 110 and no other electrodes. In FIG. 2B, a voltage is applied to electrodes 104 and 112 and in FIG. 2C, a voltage is applied to electrodes 106 and 114. In the illustrated example, the peak to crest voltage can have a value between 10 V and 500 V. The applied voltage creates a voltage profile that steps one electrode at a time to create a RTW. The voltage profile can also step two electrodes at a time, three electrodes at a time, or any arbitrary number of electrodes at a time (with of course a limitation based on the number of electrodes used). The rate at which the voltage steps forward is the RTW frequency. The effect of the RTW on ions introduced within the volume enclosed by the electrodes is to dynamically move ions backward and forward over the revolving wave, create a dynamic equilibrium for ions to remain within a certain limited volume, and prevent ions from approaching surfaces and neutralizing the ions.

In the illustrated example, each electrode receives an applied voltage periodically and a voltage is applied to each electrode in sequence. In the illustrated example, during a first time interval, a voltage is applied to electrodes 102 and 110, as shown in FIG. 2A. During a second time interval, a voltage is applied to electrodes 104 and 112 and not to electrodes 102 and 110, as shown in FIG. 2B. During a third time interval, a voltage is applied to electrodes 106 and 114, as shown in FIG. 2C. During a fourth time interval, a voltage is applied to electrodes 108 and 116 (not shown). Then, during a fifth time interval, a voltage is again applied to electrodes 102 and 110, as shown in FIG. 2A. Thus, the elevated potential continually rotates around the electrodes in a circle centered on the central axis 130. This creates a circular or rotating traveling wave of elevated potential that continually rotates or revolves around the electrodes and confines ions radially within the interior of the device 100.

In the illustrated example of FIGS. 2A-2C, during any given time interval, a voltage is applied to two electrodes positioned opposite each other (e.g., electrodes 102, 110). However, in other examples, voltages can be applied to any other combination of electrodes during each time interval, so long as the pattern of electrodes to which a voltage is applied rotates circularly. For example, a voltage could be applied to only one electrode at a time (e.g., applied to electrode 102, then 104, then 106, etc.) In another example, a voltage could be applied to two adjacent electrodes at a time (e.g., applied to electrodes 102, 104, then 104, 106, then 106, 108, etc.). In another example, voltage could be applied to three electrodes at a time (e.g., applied to electrodes 102, 104, 108, then 104, 106, 110, then 106, 108, 112, etc.) A voltage can be applied to any combination of electrodes during each time interval so long as the applied voltage rotates among the electrodes over time, ensuring that each electrode is at an elevated potential for the same amount of time in each event and on average overall.

During any given time interval, the voltage applied to some number of electrodes of the device 100 will create an elevated potential on those electrodes which will repel ions away from those electrodes. Thus, any ions near an electrode having an applied voltage will be directed away from that electrode toward the central axis 130. Then, during a later time interval, a different set of electrodes will have a voltage applied to them, which will repel ions away from that set of electrodes toward the central axis. Thus, as the applied voltage is rotated through the electrodes of the device 100, a circular traveling wave is created that constantly repels ions away from the electrodes and toward the central axis. If the speed of the rotation of the applied voltages and subsequently generated traveling wave is too slow or too fast, ions may be lost during this process. However, if the rotation of applied voltages is within an ideal frequency range, then ions will be confined within the device 100 with no loss of ions. Preferred rates of rotation are not easily determined and can depend on the particular geometry and arrangement of electrodes, the number of electrodes, the type of ions to be confined, and other factors. In addition, to the confinement of ions within the interior of the device 100, additional techniques can be used to move ions along the central axis of the device. Some of these techniques are discussed in further detail below.

Figure 2F:
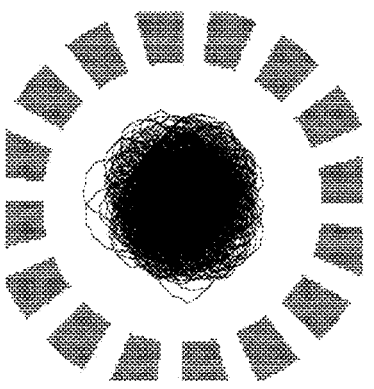
FIGS. 2D-2I show ion trajectory simulations showing ion confinement within exemplary ion manipulation devices at various pressures.
Figure 2I:
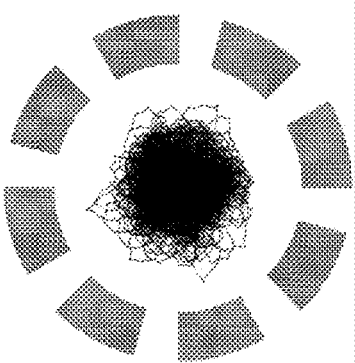
Figure 2E:
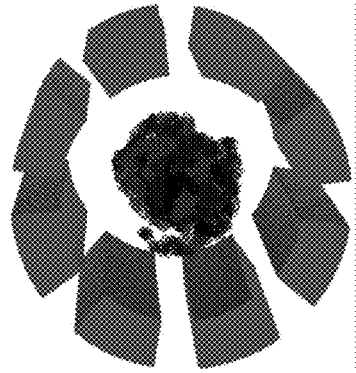
Figure 2H:
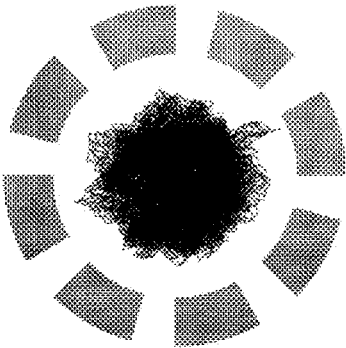
Figure 2D:
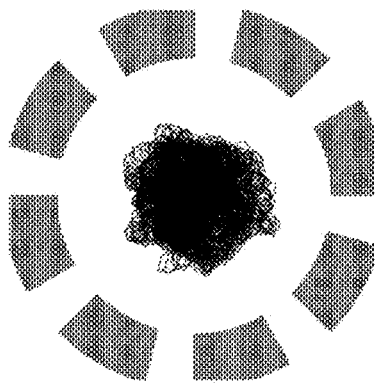
Figure 2G:
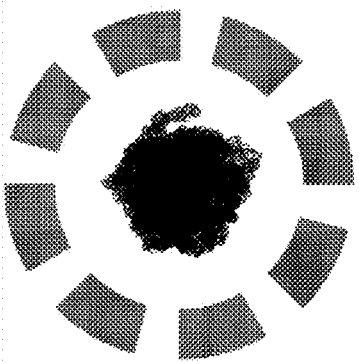

FIGS. 2D-2I show simulation results of ion confinement for other various arrangements of electrodes. FIGS. 2D and 2D show an embodiment with 8 electrodes with a travelling wave of 450 V at 50 kHz at atmospheric pressure. FIG. 2F shows an embodiment with 16 electrodes, a voltage of 300V and a traveling wave frequency of 40 kHz. FIG. 2G shows an embodiment with 8 electrodes, a voltage of 450 V, a traveling wave frequency of 40 kHz and a pressure of 1400 Torr. FIG. 2G shows an embodiment with 8 electrodes, a voltage of 150 V, a traveling wave frequency of 100 kHz, and a pressure of 100 Torr. FIG. 2I shows an embodiment with 8 electrodes, a voltage of 180 V, a traveling wave frequency of 180 kHz, and a pressure of 50 Torr. In other examples, the arrangement of electrodes can be cyclically arranged in any number of ways (e.g., circular, square, triangular, pentagonal, hexagonal, octagonal, polygonal, or any complex arrangement). FIGS. 2J-2M each show an alternative exemplary cyclical arrangement of electrodes. The electrodes in FIGS. 2J-2M can be of any dimension that will allow the creation of a revolving voltage profile within the inscribed volume to efficiently confine ions within this volume.

Figure 3:
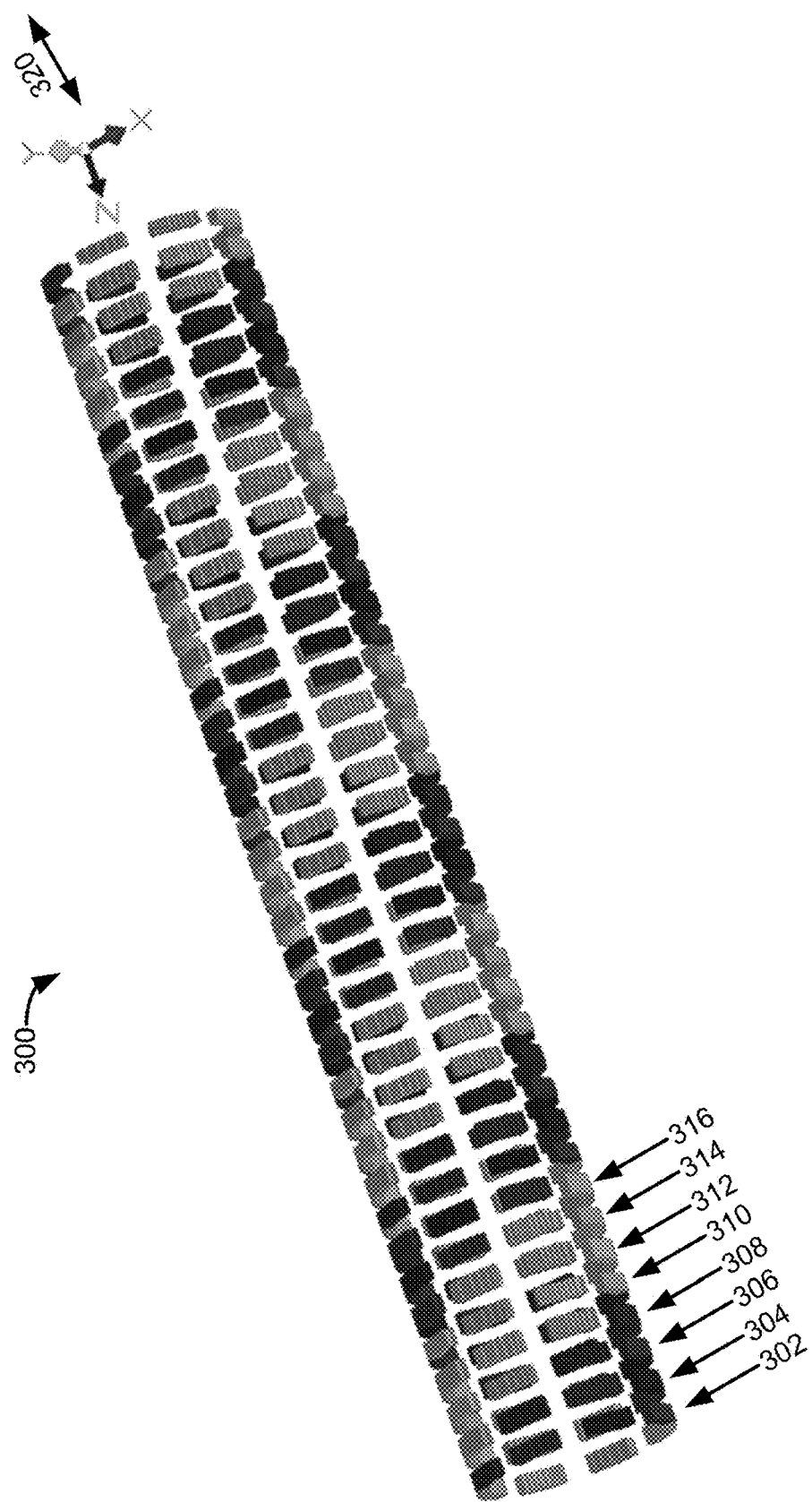
FIG. 3 is a schematic representation illustrating another exemplary embodiment of the disclosed ion manipulation devices.

FIG. 3 shows an exemplary ion manipulation device 300. In the illustrated example of FIG. 3, the device 300 includes a plurality of planar electrode rings 302, 304, 306, 308, 310, 312, 314, 316 (additional electrode rings are not labelled in FIG. 3) positioned adjacent to each other in an axial direction (e.g., along the Z-direction in the example of FIG. 3). Each electrode ring consists of a plurality of segmented electrodes arranged in a particular pattern within a plane. In the example of FIG. 3, each electrode ring is arranged in a circular pattern and the electrodes have a curvature that comports to the circular arrangement. In other examples, the electrodes can have any other shape and can be arranged in any other pattern.

Figure 4:
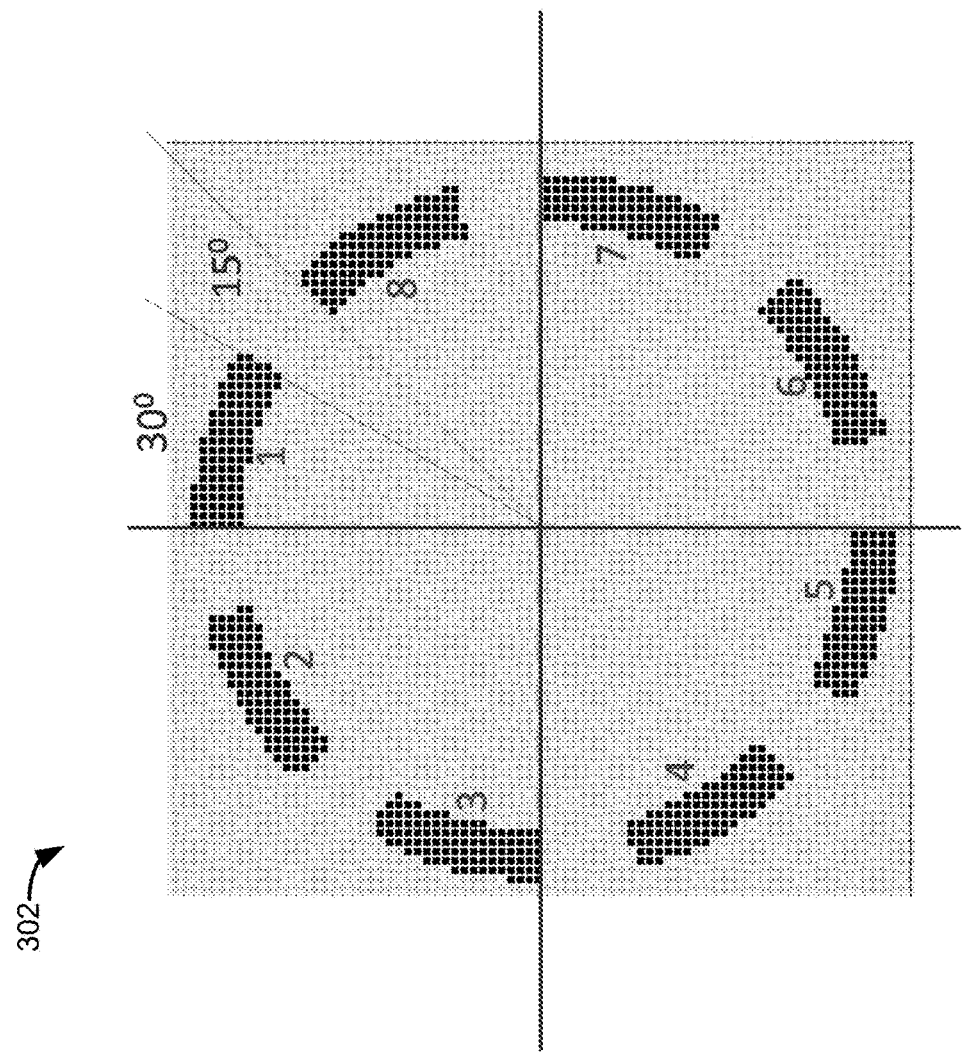
FIG. 4 is a cross-sectional view of the ion manipulation device of FIG. 3.

FIG. 4 shows a cross-sectional view of one of the electrode rings of FIG. 3. As shown in FIG. 4, the electrode ring 302 consists of eight segmented electrodes arranged in a circular pattern. Each segmented electrode spans 30° of a circle and there is a gap between each electrode that spans 15° of a circle. In other examples, there can be a different number of segmented electrodes and the size or span of the electrodes as well as the size or span of the gap between the electrodes can be different.

Referring back to FIG. 3, the rings of electrodes of device 300 can be positioned adjacent to each other such that the electrodes of each ring are axially aligned. In example of FIG. 3, there is a gap between each electrode ring. In some examples, the gap between electrodes rings can be empty space. In some examples, the gap between electrode rings can be filled with a dielectric material. In some examples, the electrode rings can be stacked directly adjacent to one another such that there is no gap between the electrode rings. The electrode rings define a central axis 320 through the device 300 (oriented in the Z-direction in FIG. 3). Ions can be guided through the interior of the device 300 along the central axis 320.

In operation, a voltage can be applied to the electrodes of each of the electrode rings of device 300 in a similar manner as described above in reference to the device 100 of FIG. 1. Each electrode of an electrode ring can periodically receive a voltage to create a potential that repels ions away from the electrode and towards the central axis 320. Any combination of electrodes in an electrode ring can have a voltage applied at any one time (e.g., a voltage can be applied to one electrode, two adjacent electrodes, two opposite electrodes, etc.). The applied voltage can them travel circularly around the electrodes of each electrode ring, thereby creating a circular traveling wave in a similar manner as discussed above in connection with FIGS. 2A-2C. As explained above, when this is done at an ideal frequency, ions can be confined within the interior of the device 300.

In the illustrated example, the same circular traveling wave is applied to each electrode ring in phase with each other electrode ring. That is, during each time interval, for each electrode of electrode ring 302 to which a voltage is applied, a voltage is also applied to each corresponding adjacent electrode in electrode rings 304, 306, etc. Additional voltages can then be applied to guide ions axially through the device as described below. In other examples, the circular traveling wave applied to each electrode ring of the device 300 is out of phase with the circular traveling wave applied to an adjacent electrode ring. The phase difference between the circular traveling waves applied to adjacent electrode rings can be between 0° and 180°. In these examples, when additional voltages are applied to guide ions axially through the device 300 as described below, the phase difference between the circular traveling waves causes ions to move through the device in a helical pattern.

In addition to the circular traveling wave created by the voltage applied to the electrodes as described above that radially confines ions, additional voltages can be superimposed on the electrodes to cause ions to move axially along the central axis 320 of the device 300 (in the Z-direction in FIG. 3). These superimposed voltages can also cause ions to separate based on their mobility as they move axially through the device 300.

In the illustrated example, an axial traveling wave can be superimposed onto the electrode rings to guide ions through the device 300. In these examples, a transient DC voltage is applied to the electrodes of a subset of the electrode rings of the device 300 and this applied voltage is then time-stepped through all of the electrode rings. For example, during a first time interval, a superimposed DC voltage can be applied to the electrodes in electrode rings 302, 304, 306, 308 and not applied to the electrodes in electrode rings 310, 312, 314, 316. During a second time interval, a superimposed DC voltage can be applied to electrode rings 304, 306, 308, 310 and during a third time interval, a superimposed DC voltage can be applied to electrode rings 306, 308, 310, 312. This can be repeated for subsequent time intervals for all the electrode rings of the device 300. This can cause an axial traveling wave to propagate along the length of the device 300, thereby creating a traveling electric field waveform that can move ions through the device. In the example just described, a transient voltage is applied to four electrode rings at a time. In other examples, the transient voltage can be applied to greater or fewer than four electrode rings at a time.

In other examples, the axial movement of ions through the device 300 can be caused by applying a DC voltage gradient to the electrode rings. In these examples, a successively lower DC voltage is applied to the electrodes in each electrode ring to create the DC gradient. For example, a superimposed voltage applied to the electrodes in ring 302 can be greater than a superimposed voltage applied to the electrodes in ring 304, which can be greater than a superimposed voltage applied to the electrodes in ring 306, etc. As such, a constant electric field is created within the interior of the device 300 that moves ions through the device.

In some examples, rather than superimposing an axial traveling wave or an axial DC voltage gradient on the electrode rings 302, 304, 306, etc., a second set of electrodes can be interleaved between the electrodes of the electrode rings. Voltages can then be applied to this additional set of segmented electrodes to guide ions axially through the device 300 via either an axial traveling wave or an axial DC voltage. For example, in the cross-sectional view shown in FIG. 4, the 15° gaps between each of the eight electrodes shown in the figure can be replaced with a second set of segmented electrodes. This can be done for each electrode ring of the device 300 such that the second set of segmented electrodes extends along the length of the device. Then, the first set of electrodes can have voltages applied to create circular traveling waves to confine ions radially, and the second set of electrodes can have voltages applied to create an axial traveling wave to guide ions axially through the device 300. In other examples, the second set of electrodes can have an axial voltage gradient applied rather than an axial traveling wave to guide the ions axially through the device.

Figure 5:
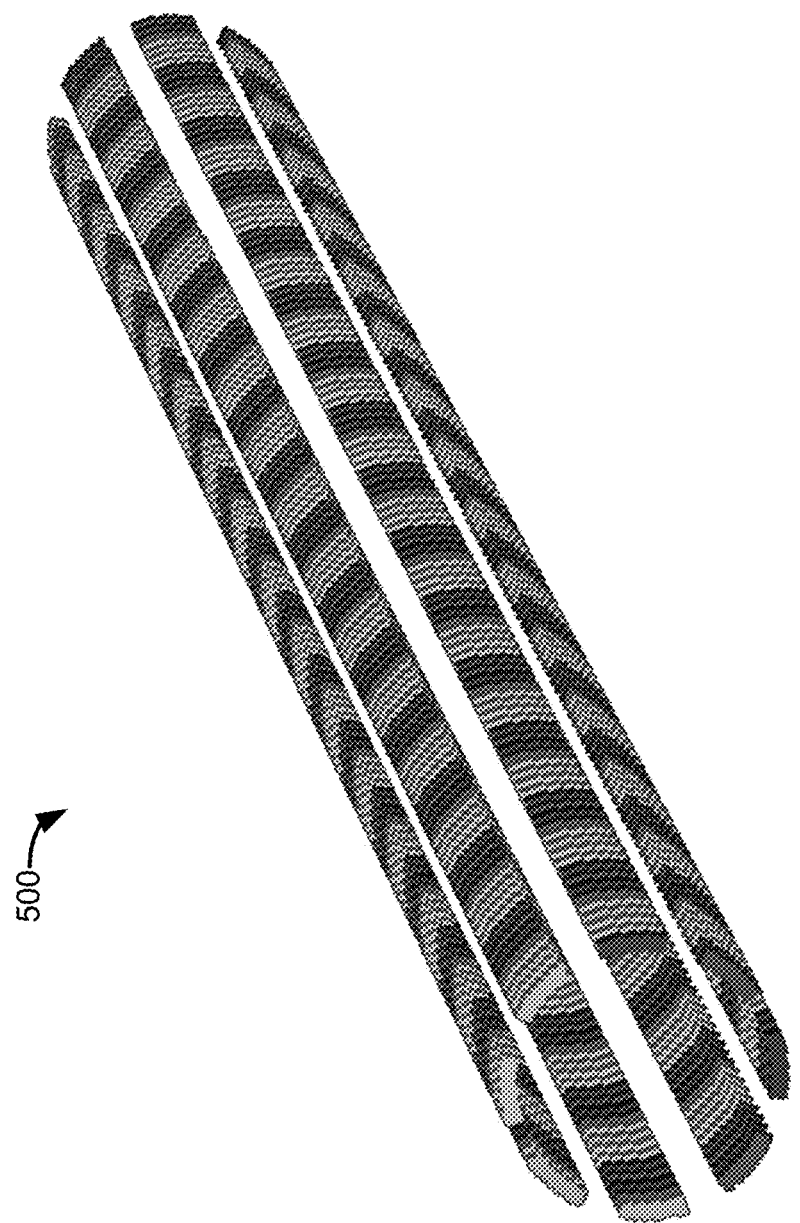
FIG. 5 is a perspective view of another exemplary embodiment of the disclosed ion manipulation devices.

FIG. 5 shows an exemplary ion manipulation device 500. Similar to the device 300 of FIG. 3, the device 500 can include a plurality of electrode rings. Each electrode ring can comprise a plurality of electrodes arranged in a particular pattern (e.g., in a circular pattern as shown in FIG. 5). The electrode rings can be positioned adjacent to each other and arranged longitudinally to define a central axis through the device 500. In the example of FIG. 5, there is no gap between each of the electrode rings. Rather, the electrode rings are stacked together directly adjacent to each other. A rotating voltage can be applied to the electrodes of the device 500 to create a circular traveling wave to radially confine ions in a similar manner as discussed above in connection with the device 300 of FIG. 3. Similarly, an axial traveling wave or a DC voltage gradient can be superimposed on the electrode rings to guide ions axially through the device 500 in a similar manner as discussed above in connection with the device 300.

Figure 6:
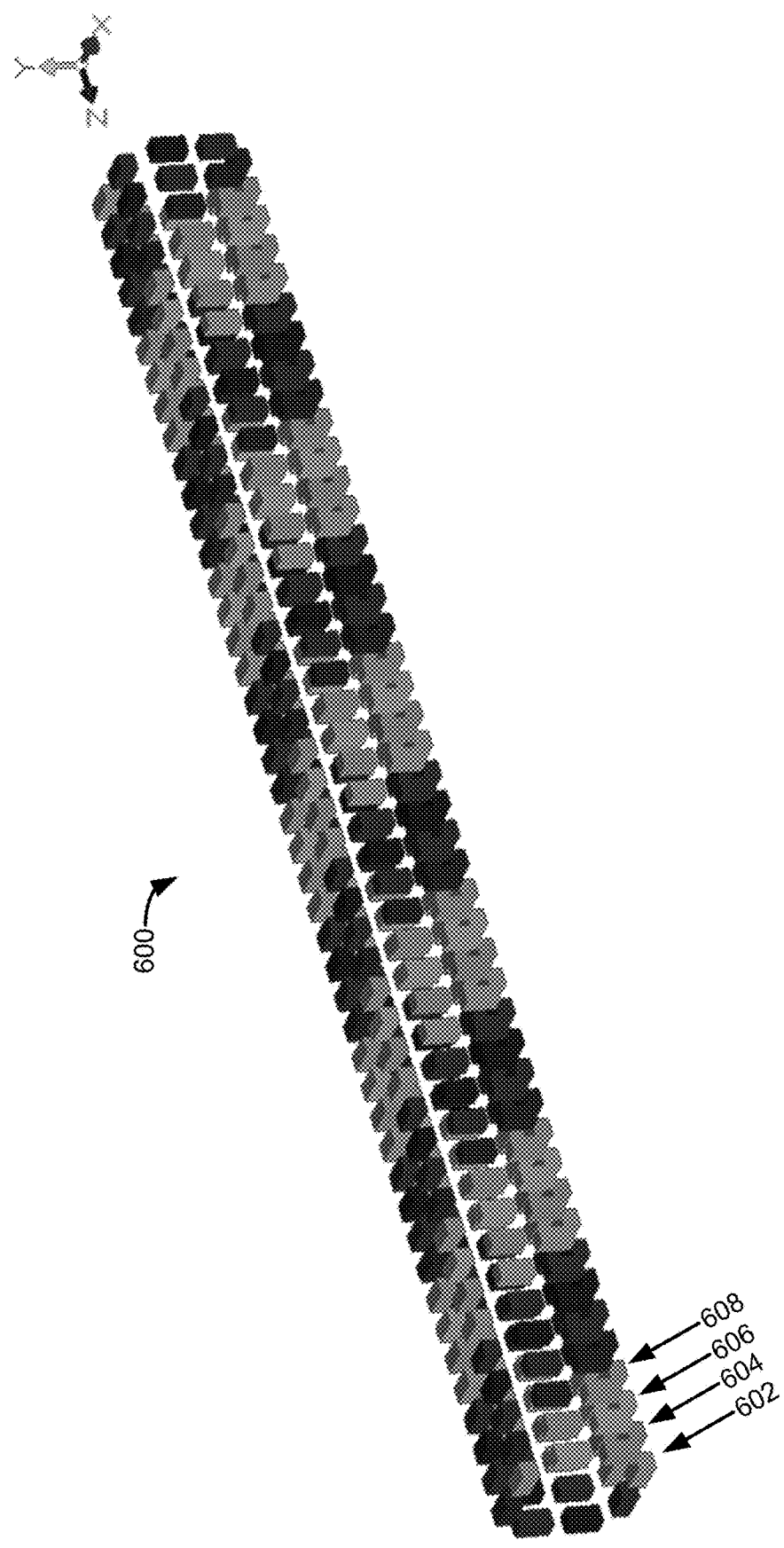
FIG. 6 is a perspective view of another exemplary embodiment of the disclosed ion manipulation devices.

FIG. 6 shows an exemplary ion manipulation device 600. In the example of FIG. 6, the device 600 can be constructed in a similar manner to the device 300 of FIG. 3 except that the electrodes of each electrode ring 602, 604, 606, etc. are straight rather than curved and the electrodes are arranged in a square pattern rather than a circular pattern. In the example of FIG. 6, each electrode ring comprises eight electrodes (e.g., two electrodes positioned on each side of the square pattern). In other embodiments, a different number of electrodes can be included in each electrode ring so long as there are at least four electrodes in each electrode ring of the device so that there can be at least one electrode on each side of the device. In some examples, the device can have a rectangular shape rather than a square shape. In these examples, there can be a different number of electrodes on the top and bottom of the device 600 than on the sides of the device. There can be a gap between each electrode of the electrode rings and there can be a gap between each electrode ring 602, 604, 606, 608.

A voltage can be periodically applied to each electrode of each electrode ring to create a circular traveling wave, in a similar manner as discussed above. This traveling wave is referred to herein as a circular traveling wave even though the movement of the traveling wave follows the square pattern of the device 600 since the traveling wave rotates around the electrodes of each electrode ring. This traveling wave can rotate around the electrodes of the electrode rings to confine ions within the interior of the device 600. As discussed above, during any given time interval, a voltage can be applied to one electrode in each electrode ring or to multiple electrodes in an electrode ring so long as the pattern of electrodes that have a voltage applied is rotated around each electrode ring. Also as discussed above, a DC voltage gradient or axial traveling wave can be superimposed on the electrode rings in order to guide ions through the device 600.

Figure 7:
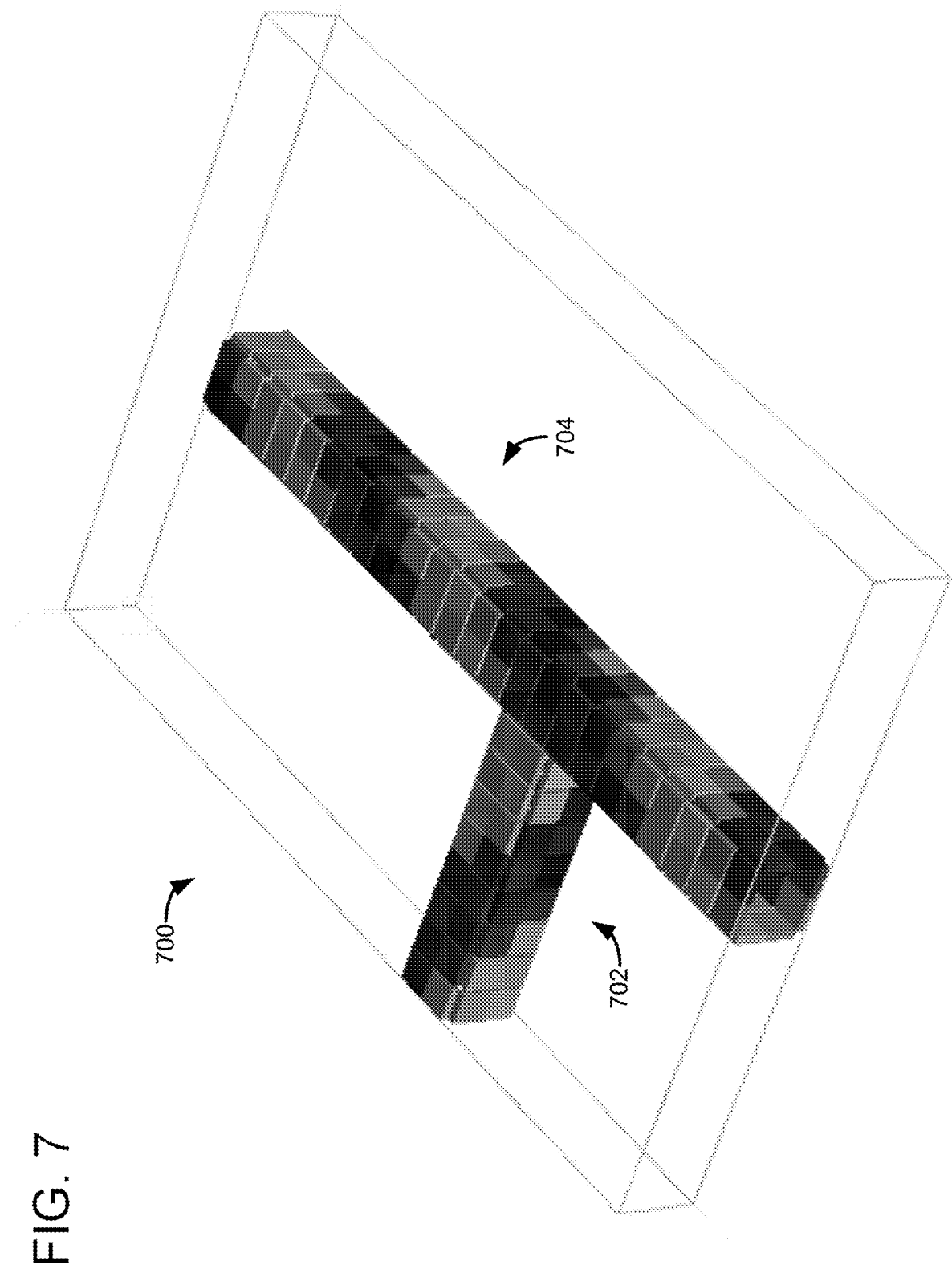
FIG. 7 is a perspective view of another exemplary embodiment of the disclosed ion manipulation devices that have a T-shaped configuration.

FIG. 7 shows an exemplary ion manipulation device 700. In the example of FIG. 7, the device 700 can include a first portion 702 and a second portion 704 arranged in a substantially T-shaped configuration, allowing ions to be switched at a junction of the first and second portions. The device 700 can further include a switch (not shown in FIG. 7) or similar mechanism that can cause ions to move in a straight path along portion 704 or to curve or bend at the junction with the first portion 702 and thereby travel along the first portion.

In the illustrated example of FIG. 7, each of the first portion 702 and the second portion 704 are constructed in a similar manner to the device 600 of FIG. 6, wherein they comprise a plurality of electrode rings with each electrode ring being arranged in a square pattern and there are gaps between the electrode rings. In other examples, the electrodes of each electrode rings can be arranged in other patterns (e.g., a circular pattern similar to FIG. 3) and there can be a gap between each electrode ring. The switch between the first portion 702 and the second portion 704 of the ion manipulation device 700 allows for more control of ions and more potential applications for the device. Ions can be contained within the first portion 702 and the second portion 704 by applying a circular traveling wave caused by a rotating voltage applied to the electrodes of each electrode ring as described above with respect to other embodiments. In other embodiments, the first and second portions 702, 704 can be arranged to form a substantially Y-shaped configuration, a substantially X-shaped configuration, or a substantially multidirectional shape with multiple junction points allowing ions to be switched at a junction to one or more sides of the configuration.

Figure 8:
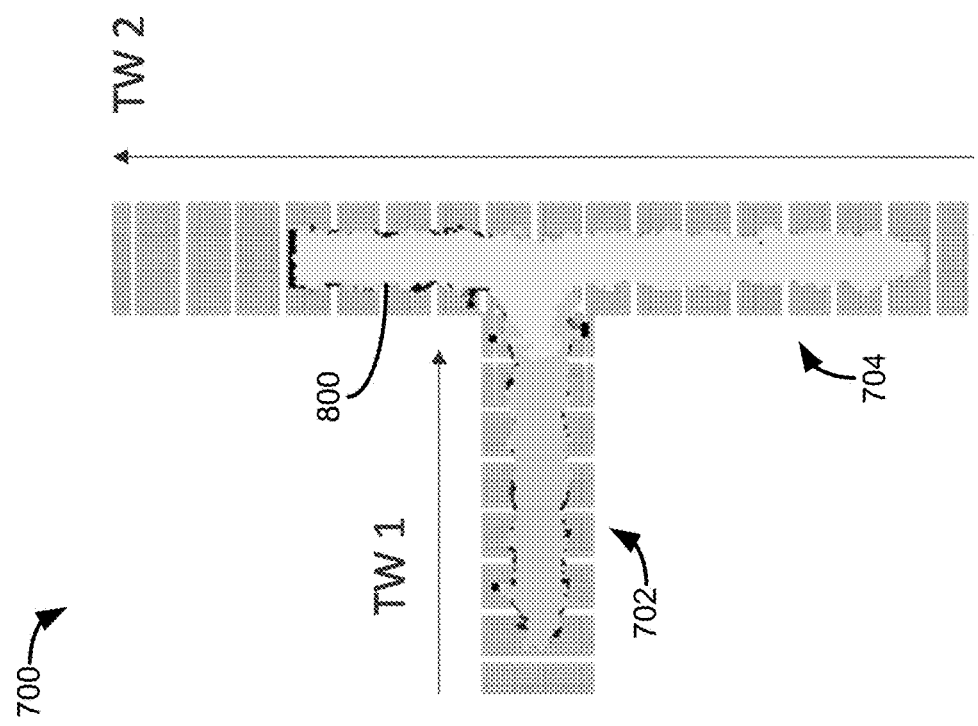
FIG. 8 is a schematic representation of the ion manipulation device of FIG. 7.
Figure 9B:
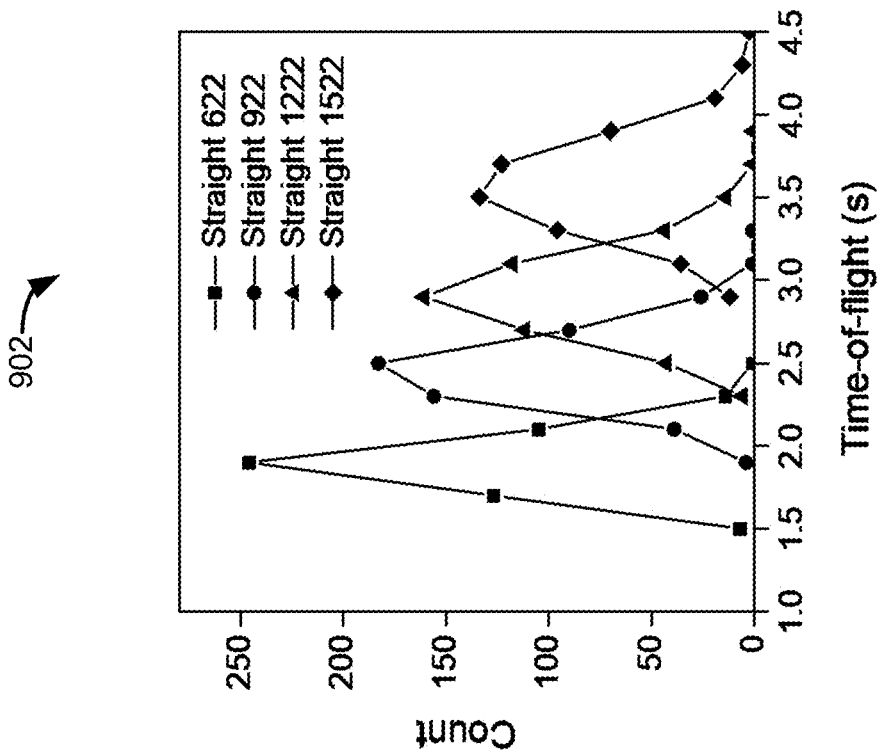
FIGS. 9A-9B show plots of simulation results of ions traveling through the ion manipulation device of FIGS. 7-8.
Figure 9A:
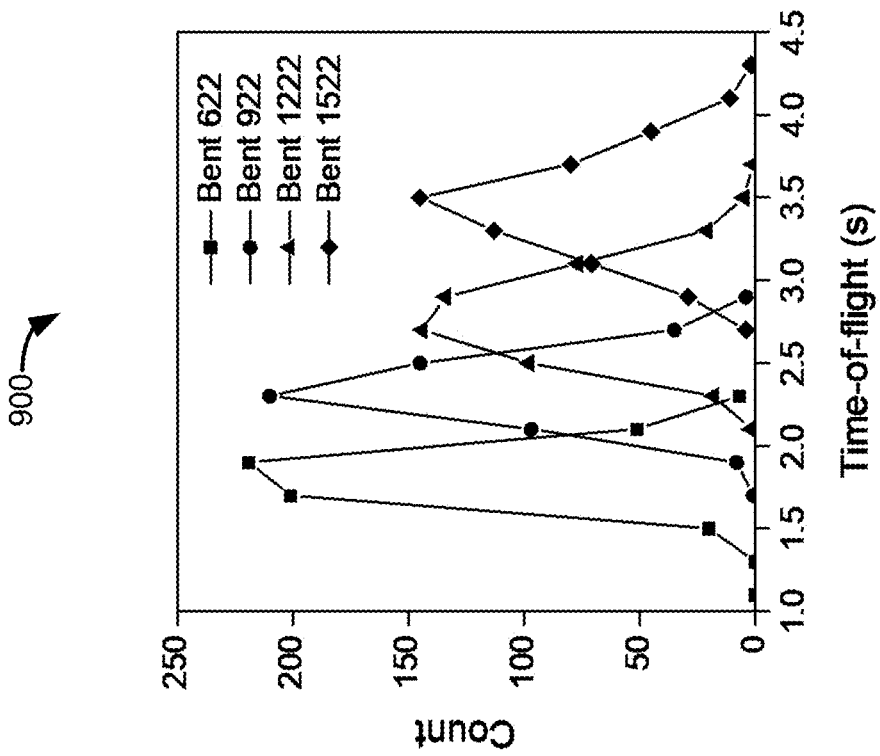

FIG. 8 shows a simulation of an ion switch of the T-shaped device 700 of FIG. 7 and an ion cloud 800. The path of the ion cloud 800 can be controlled using switch elements as described above. A first traveling wave TW1 can guide ions along the first portion 702 and a second traveling wave TW2 can guide ions along the second portion 704. FIGS. 9A and 9B show simulation results of ions traveling in device 700 of FIG. 7. These simulations results were obtained using SIMION® software. FIG. 9A shows a plot 900 of simulation results of ions traveling along the bent path as shown in FIG. 8 and FIG. 9B shows a plot 902 of simulation results of ions traveling along the straight path as shown in FIG. 8. FIG. 9A and FIG. 9B show plots of ion count vs. time of flight for four different masses of ions.

FIGS. 10A and 10B shows plan views of an ion manipulation device 1000. FIGS. 10C and 10D show cross-sectional views of the device 1000. The device 1000 includes two substantially parallel surfaces 1002, 1004. FIGS. 10A, 10B show the upper surface 1002. The lower surface 1004 is constructed similarly to the upper surface 1002. The device 1000 contains a central or longitudinal axis 1070 along which ions can be guided between the upper and lower surfaces 1002, 1004.

Each surface 1002, 1004 of the device 1000 includes a plurality of outer guard electrodes on either side of the surface and a plurality of confinement electrodes 1050 arrayed along the center of the surface. In the illustrated example, the upper surface 1002 contains eight guard electrodes including four guard electrodes 1010, 1012, 1014, 1016 on one side of the surface and four guard electrodes 1018, 1020, 1022, 1024 on the other side of the surface. The lower surface 1004 similarly contains eight guard electrodes.

In the illustrated example, each guard electrode is elongated along the length of the device 1000. In other examples, each of the guard electrodes 1010-1024 and 1030-1044 can be broken up into multiple electrodes with each electrode extending partially along the length of the device 1000 such that the combined length of the guard electrodes spans the length of the device. In such examples where a guard electrode is broken into multiple electrodes, there may be gaps along the axial direction of the central axis 1070 between such electrodes.

The guard electrodes can direct ions away from the edges or sides of the device 1000 and keep ions contained near the center of the device. In the illustrated example, each set of guard electrodes creates a guard traveling wave as described herein. A guard traveling wave can be created by sequentially applying a transient DC voltage to adjacent guard electrodes. For example, during a first time interval, a voltage can be applied to electrodes 1024 and 1044, during a second time interval, a voltage can be applied to electrodes 1022 and 1042, during a third time interval, a voltage can be applied to electrodes 1020 and 1040, and during a fourth time interval, a voltage can be applied to electrodes 1018 and 1038. During a fifth time interval, a voltage can be again applied to electrodes 1024 and 1044 and this cycle can be repeated. Thus, a traveling wave can be created that guides ions from the edges of the device 1000 towards the center of the device 1000. A similar traveling wave can be created with electrodes 1010, 1012, 1014, 1016, 1030, 1032, 1034, 1036. In some examples, the traveling wave can be created by applying a voltage to multiple guard electrodes simultaneously. For example, during a first time interval, a voltage can be applied to electrodes 1022, 1024, 1042, 1044, during a second time interval, a voltage can be applied to electrodes 1020, 1022, 1040, 1042, etc. In some examples, a constant DC voltage can be applied to the guard electrodes rather than a traveling wave. This creates an electric field that forces ions towards the center of the device.

The confinement electrodes 1050 can comprise a plurality of electrode rows on each of the upper and lower surfaces 1002, 1004. The electrode rows can be positioned adjacent to each other along the direction of the central axis 1070 and each electrode row can comprise a plurality of electrodes positioned next to each other. In some examples, there is a gap between each electrode row. In some examples, there is a dielectric material between each electrode row. In some examples, the electrode rows are positioned directly adjacent to each other with no gap between them. As shown in FIGS. 10A, 10B, the electrode rows 1050 can extend along the entire length of the device 1000 and can be radially positioned in between the guard electrodes 1010-1024. In the illustrated example, each electrode row comprises four electrodes. In other examples, each electrode row can comprise greater than four electrodes or as few as two electrodes.

The cross-sectional view of FIGS. 100, 10D show one electrode row on each of the upper and lower surfaces 1002, 1004. The electrode row on the upper surface 1002 comprises electrodes 1052, 1054, 1056, 1058 and the electrode row on the lower surface 1004 comprises electrodes 1062, 1064, 1066, 1068. For each confinement electrode on the upper surface 1002, there is a corresponding confinement electrode directly across on the lower surface 1004. For example electrode 1052 on the upper surface 1002 is directly across from electrode 1062 on the lower surface 1004. In the illustrated example, there are four confinement electrodes in each electrode row on the upper surface 1002 and four confinement electrodes in each electrode row on the lower surface 1004. However, in other examples, there can be more than four electrodes or as few as two electrodes in each electrode row.

Each of the confinement electrodes can receive a voltage to create a potential that can repel ions away from the electrode and towards the longitudinal or central axis 1070 of the device 1000. A voltage can be periodically applied to each of the confinement electrode and the applied voltage rotated among each of those electrodes in a similar manner as discussed above in connection with FIGS. 2A-2C. For example, during a first time interval a voltage can be applied to electrode 1052, during a second time interval a voltage can be applied to electrode 1054, and in subsequent time intervals a voltage can be applied to electrodes 1056, 1058, 1068, 1068, 1066, 1064, 1062 sequentially. This can create a circular traveling wave that can confine ions between the parallel surfaces 1002, 1004 as the ions are guided along the longitudinal axis. Multiple confinement electrodes can have a voltage applied simultaneously so long as the pattern of voltages applied to the electrodes rotates among the electrodes sequentially as illustrated by the circular arrows shown in FIG. 10A.

Figure 11:
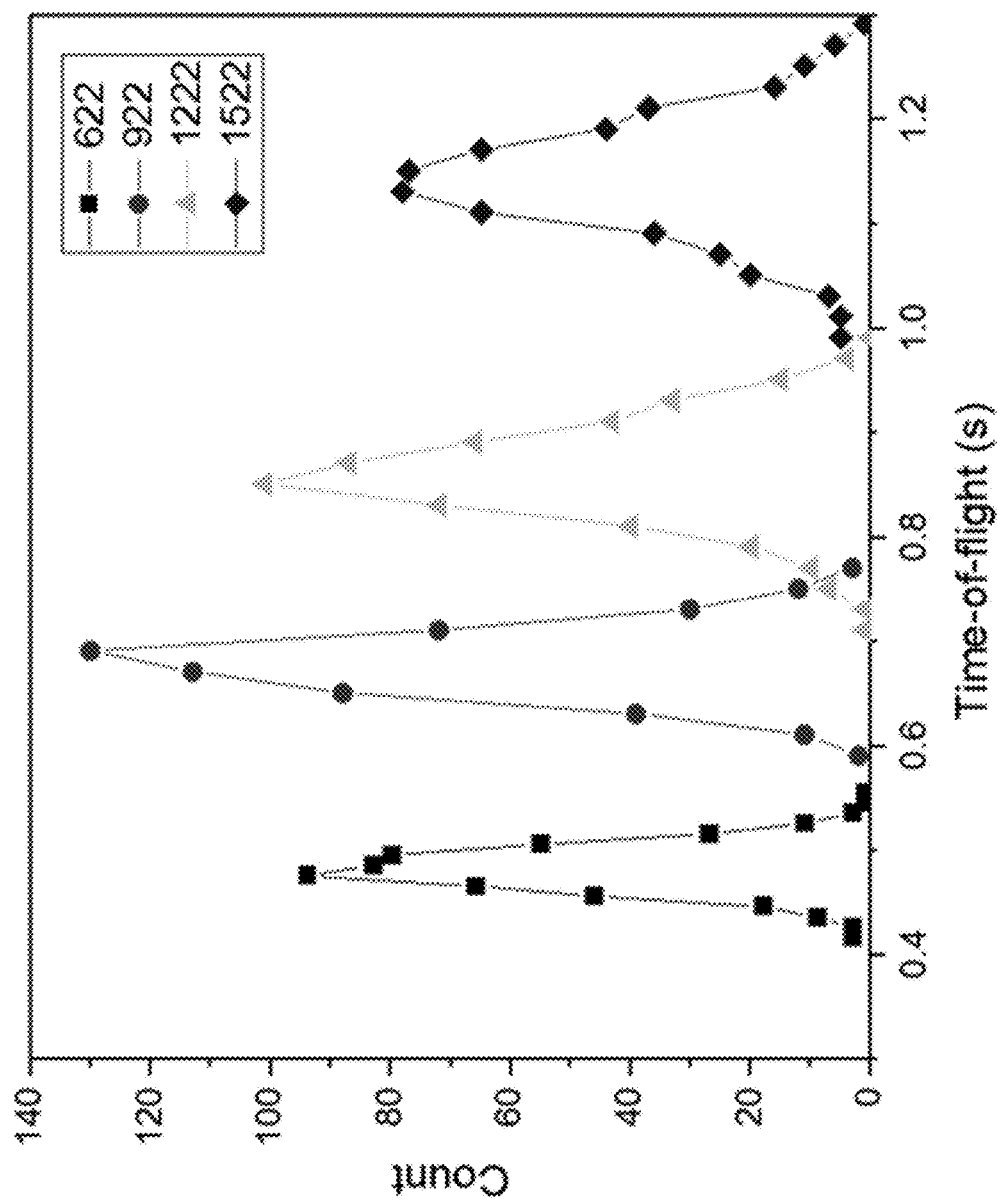
FIG. 11 shows a plot of simulation results of ions traveling through the ion manipulation device of FIGS. 10A-10D.

FIGS. 10B and 10D show an ion cloud 1080 confined between the two surfaces 1002, 1004. The guard electrodes keep the ions of the ion cloud 1070 away from the edges and towards the center of the device 1000 and the traveling wave of the confinement electrodes keep the ions between the surfaces 1002, 1004 with little or no ion loss. Thus, the ion cloud 1080 can be guided along the longitudinal axis of the device 1000 with little or no ion loss. FIG. 11 shows a plot 1100 simulation results of ions traveling in the device 1000 of FIGS. 10A-10D. FIG. 11 shows time of flight of ions having different masses.

Figure 12B:
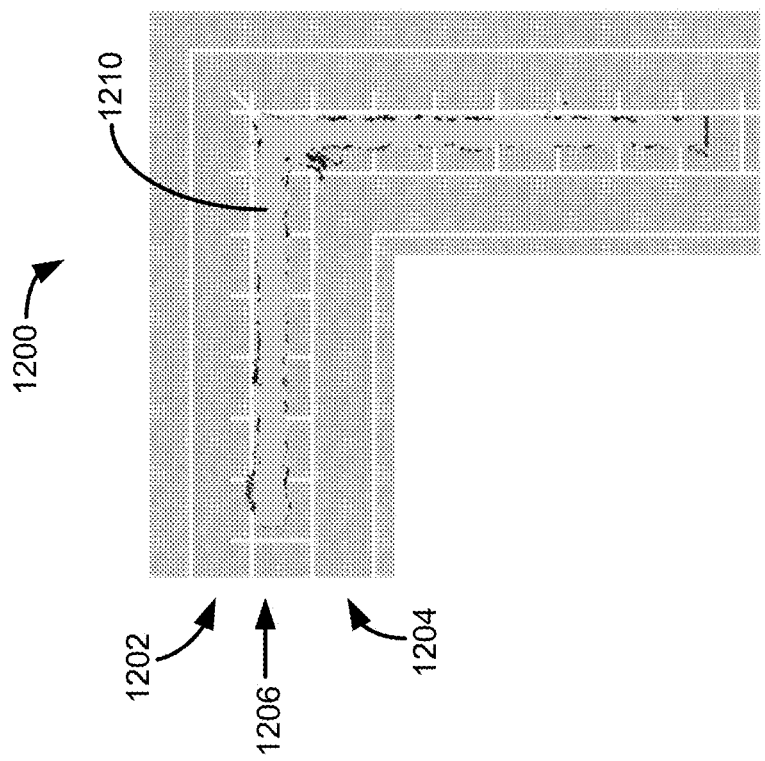
FIGS. 12A-12B show schematic representations illustrating another exemplary embodiment of the disclosed ion manipulation devices.
Figure 12A:
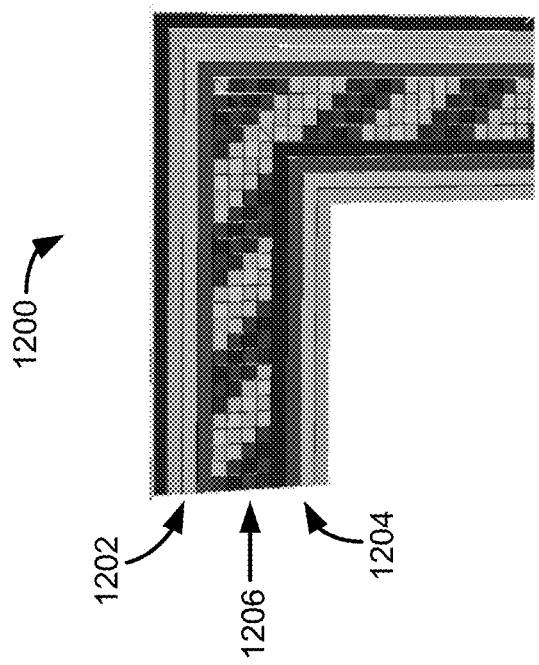
Figure 13:
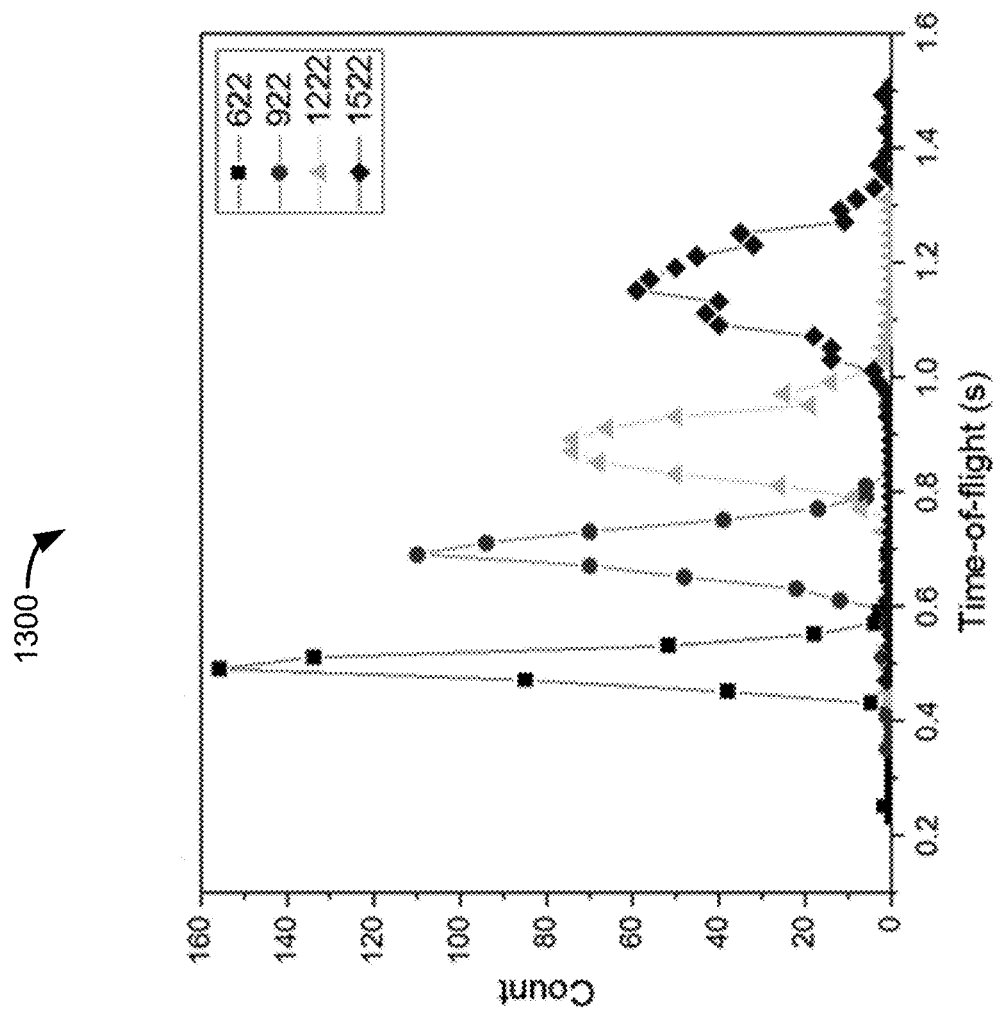
FIG. 13 shows a plot of simulation results of ions traveling through the ion manipulation device of FIGS. 12A-12B.

FIGS. 12A, 12B show an exemplary ion manipulation device 1200. The device 1200 is similar to the device 1000 except that the device 1200 contains a corner with a 90° turn. This allows for ions to travel a more serpentine pattern in a confined space. Similar to the device 1000, the device 1200 comprises two parallel surfaces such that ions can be guided between the surfaces. FIG. 12A shows one such surface. The surface shown in FIG. 12A can comprise outer guard electrodes 1202, 1204, similar to guard electrodes 1010-1024 of device 1000 and confinement electrodes 1206, similar to confinement electrodes 1050 of device 1000. In the illustrated example, each surface of the device 1000 comprises four elongated guard electrodes on one side of the device, four elongated guard electrodes on the other side of the device, and an array of electrode rows positioned in between the guard electrodes, wherein each electrode row consists of four electrodes positioned next to each other. In other examples, there can be any other number of guard electrodes and/or electrodes per electrode row. FIG. 12B shows the device 1200 and a simulation of an ion cloud 1210 advancing through the device 1200. As can be seen in FIG. 12B, ions can turn around the corner of the device. FIG. 13 shows a plot 1300 of simulation results of ions traveling in the device 1200.

Figure 14:
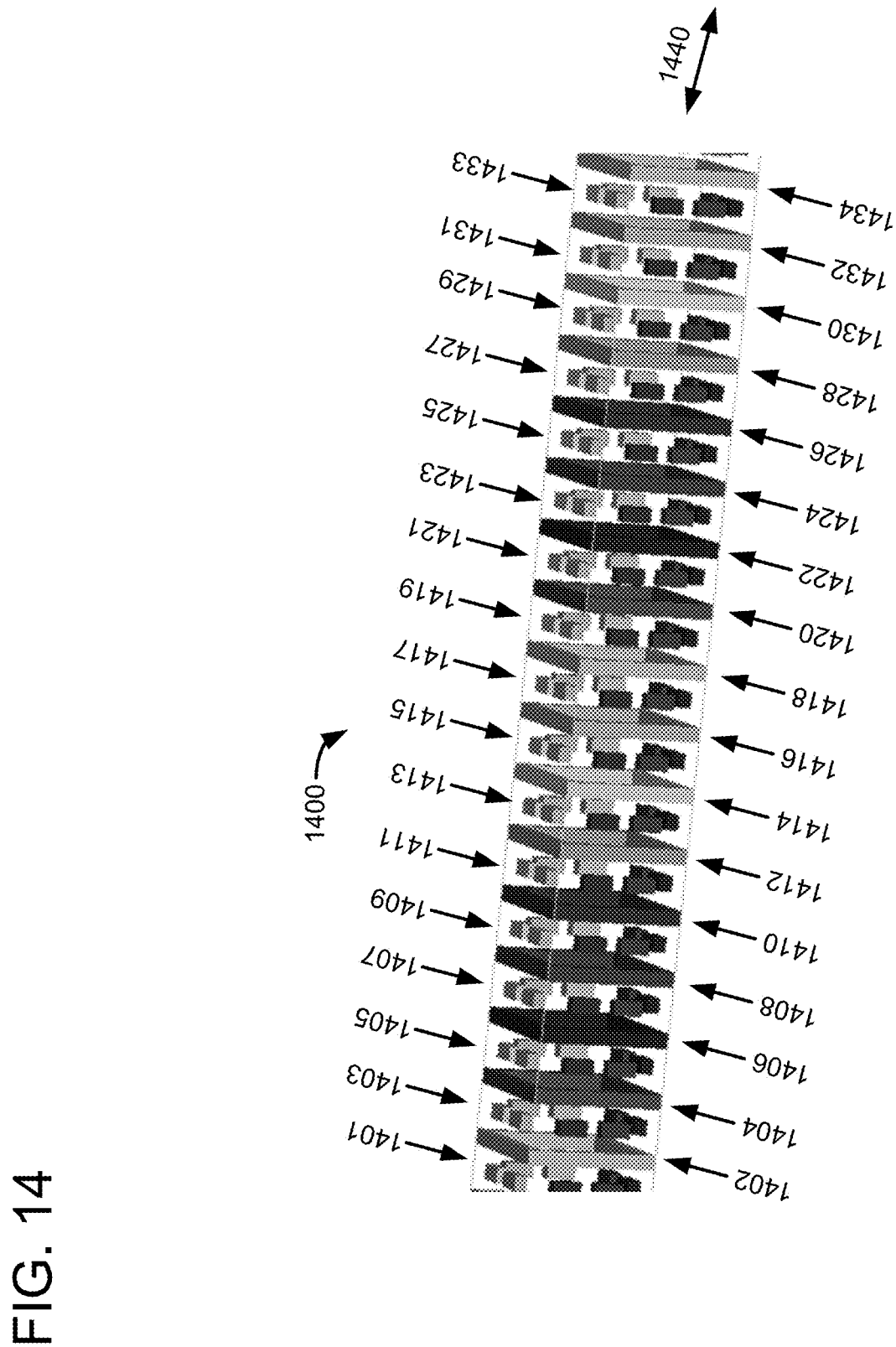
FIG. 14-16 show various views of another exemplary embodiment of the disclosed ion manipulation devices.

FIG. 14 shows an exemplary ion manipulation device 1400. The device 1400 includes a plurality of electrode rings 1401, 1403, 1405, etc., and a plurality of unsegmented electrodes 1402, 1404, 1406, etc., alternately interspersed. The electrode rings can be similar to electrode rings 302, 304 of FIG. 3 and can comprise a plurality of segmented electrodes arranged in a particular pattern. In the illustrated example of FIG. 6, the electrode rings consist of eight segmented electrodes arranged in a square pattern (e.g., two electrode on each of four side). In other examples, any other number of electrodes can be used and they can be arranged in any pattern (e.g., a circular pattern).

In the illustrated example, the unsegmented electrodes are shaped as a square. In other examples, the unsegmented electrodes can have any other shape (e.g., circular). In the illustrated example, voltages can be applied to the segmented electrodes of the electrode rings to confine ions within the device 1400 and voltages can be applied to the unsegmented electrodes to guide the electrodes along the length of the device. The voltages applied to the electrodes of the electrode rings 1401, 1403, etc. can rotate around the electrodes or each electrode ring to create a circular traveling wave in a similar manner as discussed above with respect to FIG. 6. This circular traveling wave can confine electrodes within the device 1400 with little or no ion loss.

In the illustrated example, the voltages applied to the unsegmented electrodes 1402, 1404 can create an axial traveling wave along the direction of the longitudinal axis 1440 that can move ions through the device 1400. For example, during a first time interval, a voltage can be applied to electrodes 1402, 1404, 1406, during a second time interval, a voltage can be applied to electrodes 1404, 1406, 1408, during a third time interval, a voltage can be applied to electrodes 1406, 1408, 1410, etc. Thus, a traveling electric field waveform can guide through the device 1400 along the longitudinal axis 1440.

In other examples, a DC voltage gradient can be created along the unsegmented electrodes. For example, a voltage can be applied to electrode 1402, which can be greater than a voltage applied to electrode 1404, which can be greater than a voltage applied to electrode 1406, etc. This can create a constant electric field that guides ions through the device 1400 along the longitudinal axis 1440.

Figure 15:
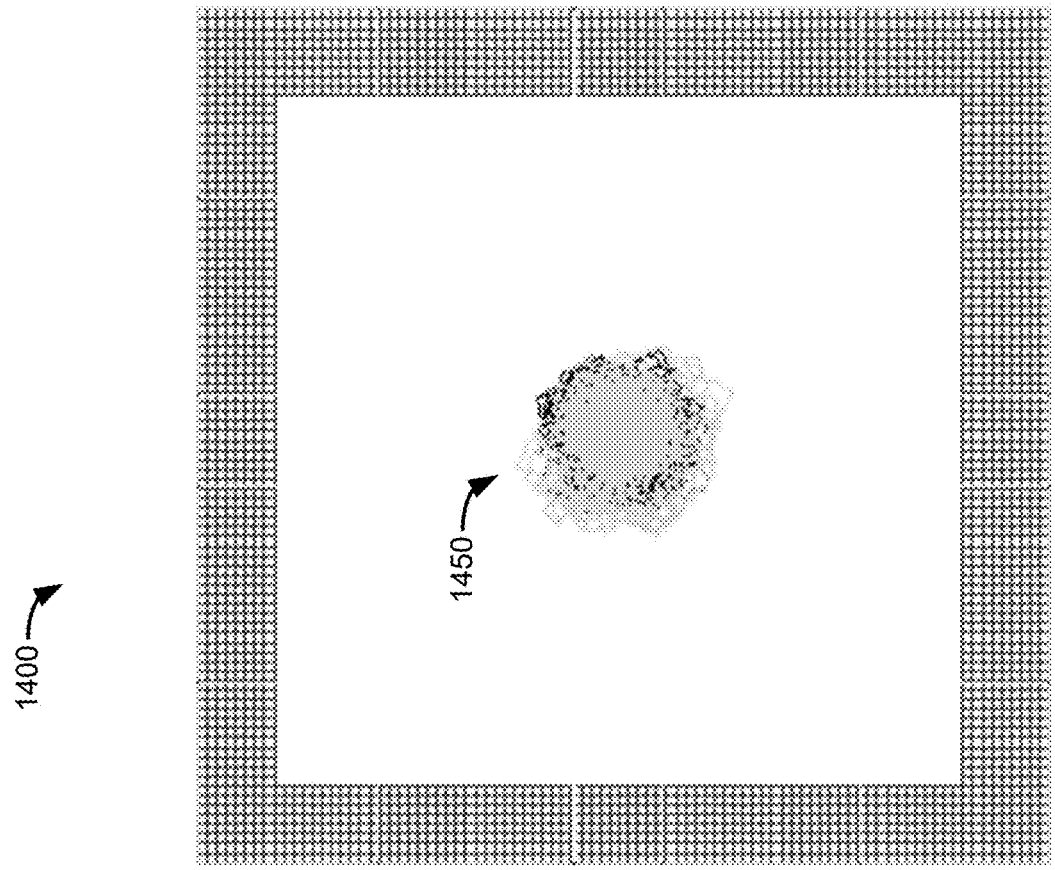
Figure 16:
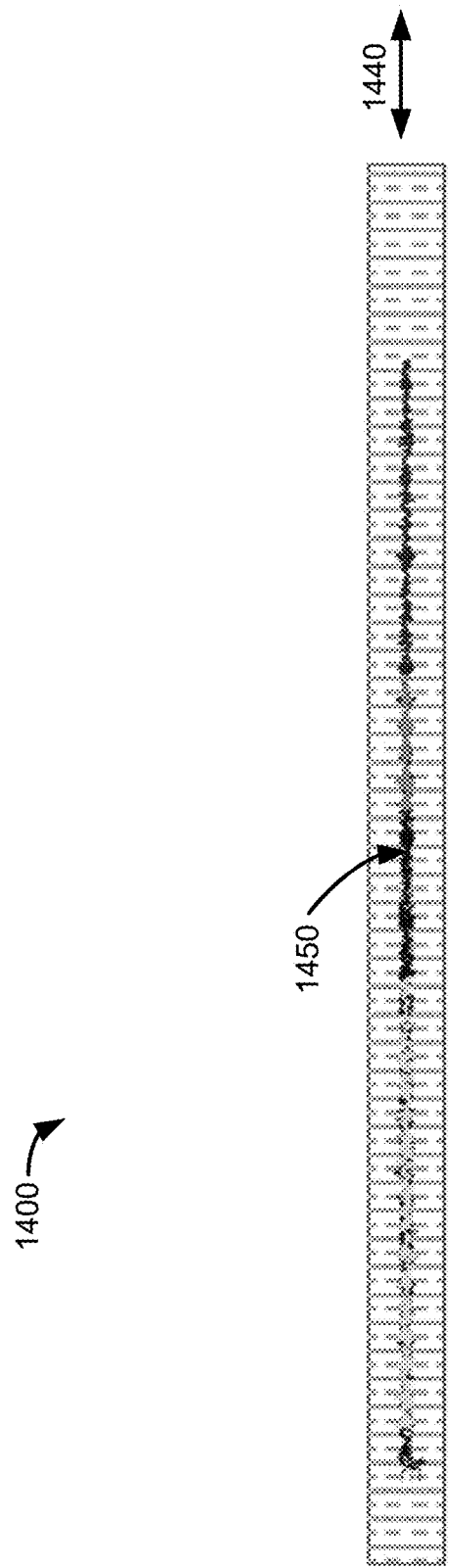
Figure 17:
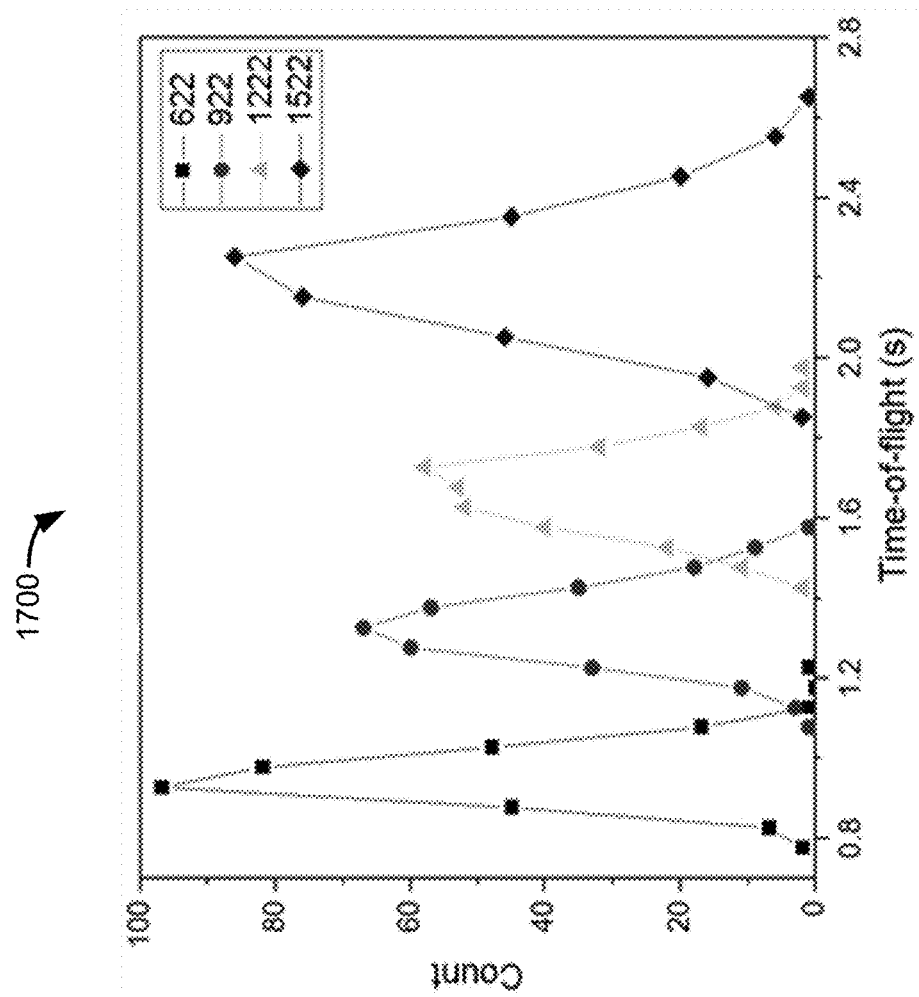
FIG. 17 shows a plot of simulation results of ions traveling through the ion manipulation device of FIGS. 14-16.

FIG. 15 shows a cross-sectional view of the device 1400 of FIG. 14 and an ion cloud 1450 confined near the central axis 1440 of the device. FIG. 16 shows a plan view of the device 1400 of FIG. 14 and the ion cloud 1450 moving through the device along the central axis 1440 of the device. FIG. 17 shows a plot 1700 with simulation results of ions traveling through the device 1400 of FIG. 14.

Figure 18A:
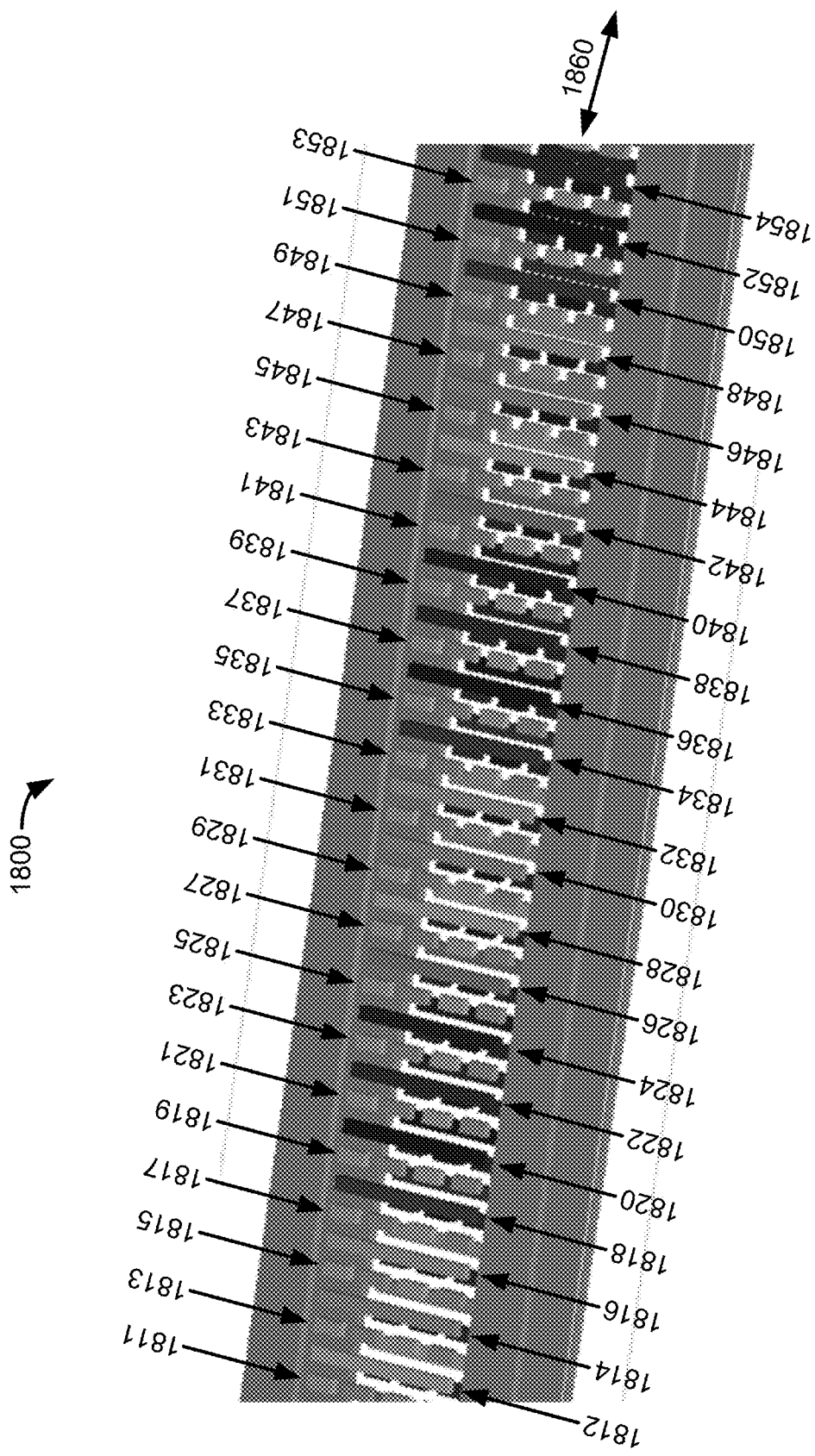
FIGS. 18A-18C show various views of another exemplary embodiment of the disclosed ion manipulation devices.
Figure 18B:
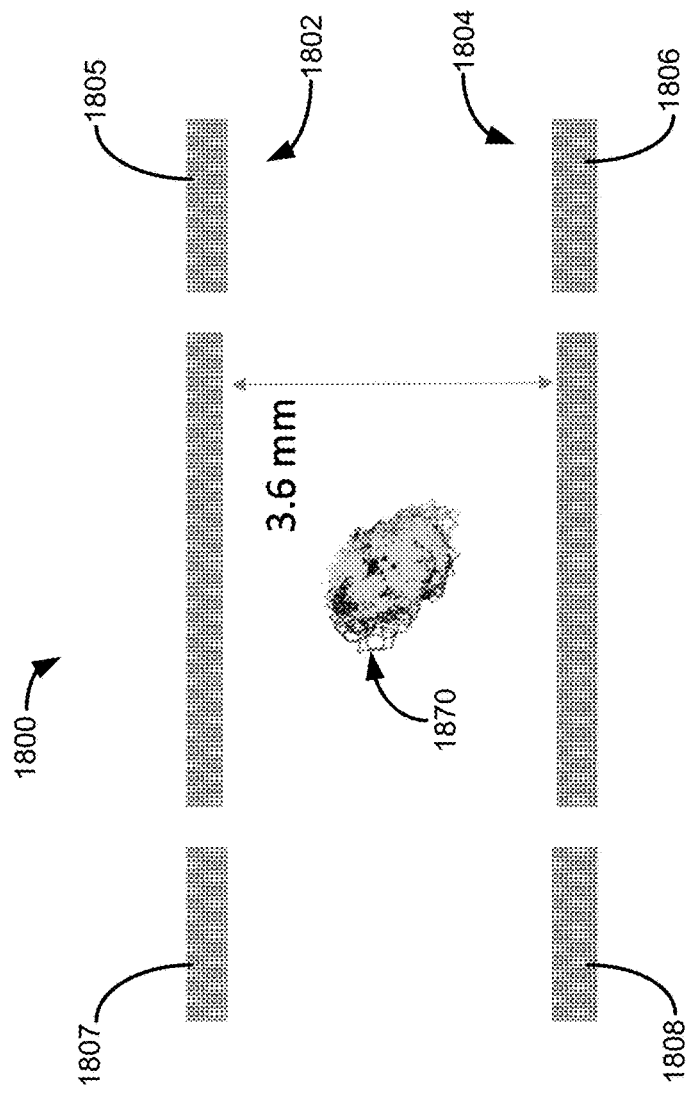
Figure 18C:
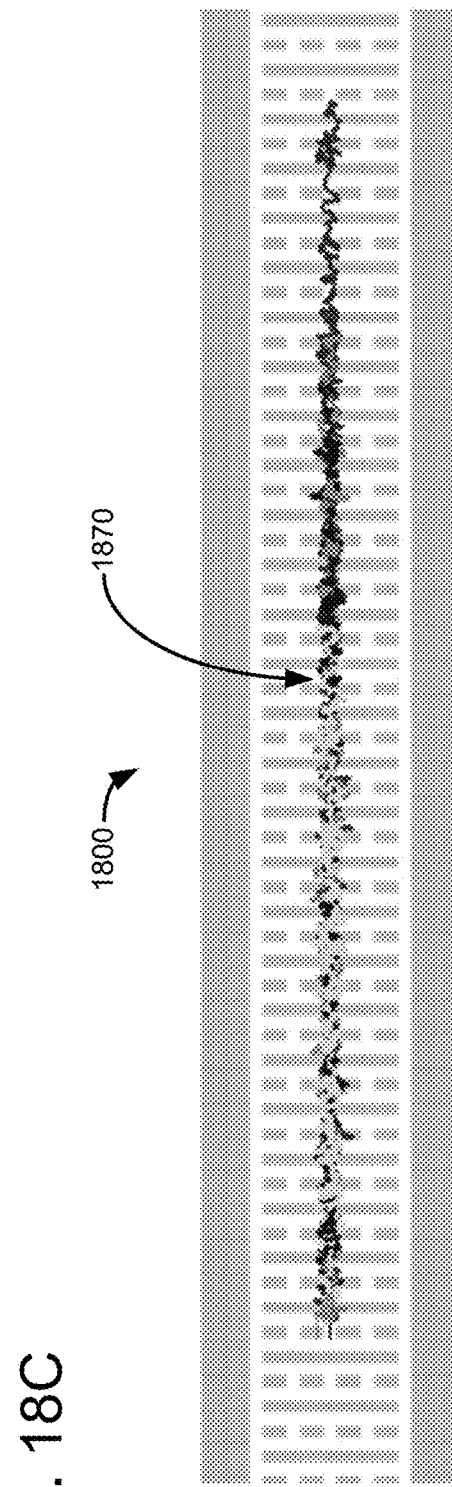

FIGS. 18A-18C show an exemplary ion manipulation device 1800. FIG. 18A shows a perspective view of the device 1800, FIG. 18B shows a cross-sectional view of the device, and FIG. 18C shows a plan view of the device. The device 1800 consists of two parallel surfaces 1802 and 1804 separated by a short distance. The distance between the surfaces 1802, 1804 is preferably between 0.5 mm and 10 mm and more preferably between 2 mm and 5 mm and, in certain embodiments, is 3.6 mm. Each surface 1802, 1804 of the device 1800 comprises outer guard electrode and confinement ions positioned between the guard electrodes. Each of the guard electrodes 1805, 1806, 1807, 1808 can be an elongated electrode that extends across the entire length of the device 1800. A DC voltage can be applied to each of the guard electrodes to create an electric field near the edges of the device 1800 that can confine ions to the center of the device between the confinement electrodes. In some examples, each of the guard electrodes 1805, 1806, 1807, 1808 can be replaced with multiple elongated electrodes positioned next to each other. In these examples, a transient DC voltage can be applied to these guard electrodes to create a traveling wave to confine ions to the center of the device in a similar manner as described above in connection with FIGS. 10A-10D.

The confinement electrodes on each surface of the device 1800 include a plurality of segmented electrode rows and a plurality of unsegmented electrodes alternately interspersed with each other. For example, as shown in FIG. 18A, the upper surface of the device 1800 consists of electrode row 1811, next to unsegmented electrode 1812, next to electrode row 1813, next to unsegmented electrode 1814, etc. There can be a gap between each electrode ring and an adjacent unsegmented electrode. Each electrode ring comprises a plurality of segmented electrodes positioned in a row. In the illustrated example, each electrode row contains four such segmented electrodes. In other examples, each electrode row can contain more or less than four segmented electrodes. Each unsegmented electrode can be positioned to span between the outer guard electrodes such that the length of each unsegmented electrode is the same or is about the same as the length of each electrode row.

One or more voltages can be applied to the electrodes of the electrode rings to confine ions between the surfaces 1802, 1804 and one or more voltages can be applied to the unsegmented electrodes to guide ions through the device 1800 along the longitudinal axis 1860. The voltage applied to the electrodes in the electrode rows can be alternated among the electrodes in a rotating pattern to create a rotating traveling wave in a similar manner as described with respect to the electrodes 1050 discussed above in connection with FIGS. 10A-10D. This traveling wave can confine ions between the parallel surfaces 1802, 1804.

In the illustrated example, voltages are applied to the unsegmented electrode to create an axial traveling wave oriented along the direction of the longitudinal axis 1860 to guide ions through the device 1800 between the surfaces 1802, 1804. These voltages applied to the unsegmented electrodes can be a transient DC voltage profile, in a similar manner as discussed above in connection with the unsegmented electrodes of FIG. 14. For example, in a first time interval, a voltage can be applied to electrodes 1812, 1814. Then, in a second time interval, a voltage can be applied to electrodes 1814, 1816, and so on. The number of unsegmented electrodes to which a voltage is applied at any given time can be any number so long as the electrodes to which a voltage is applied moves along the direction of the longitudinal axis 1860 over time. This can create a traveling wave that causes ions to move through the device 1800 along the direction of the longitudinal axis 1860.

Figure 19:
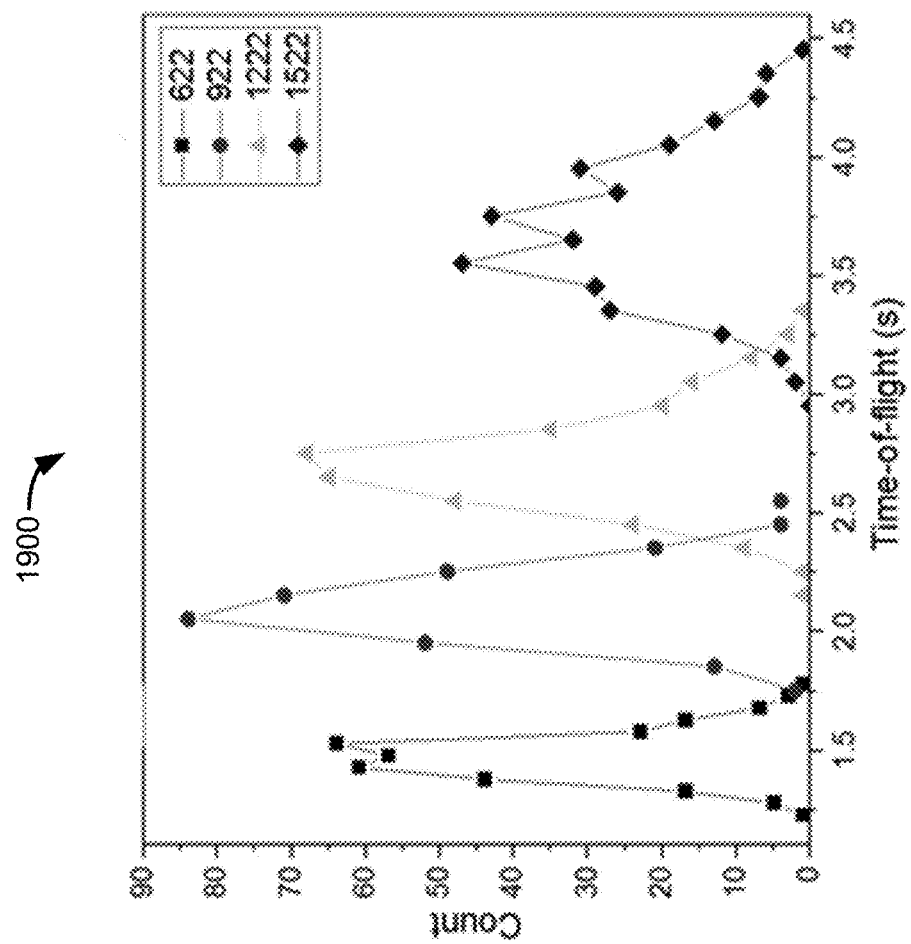
FIG. 19 shows a plot of simulation results of ions traveling through the ion manipulation device of FIGS. 18A-18C.

In another example, voltages can be applied to the unsegmented electrodes to create a DC voltage gradient. For example, a voltage applied to electrode 1812 can be greater than the voltage applied to electrode 1814, which can be greater than the voltage applied to electrode 1816, and so on. This can create a fixed voltage drop along the length of the device 1800 that can cause ions to move through the device. FIG. 19 shows a plot 1900 containing simulation results of ions traveling through the device 1800 of FIGS. 18A-18C.

Figure 20:
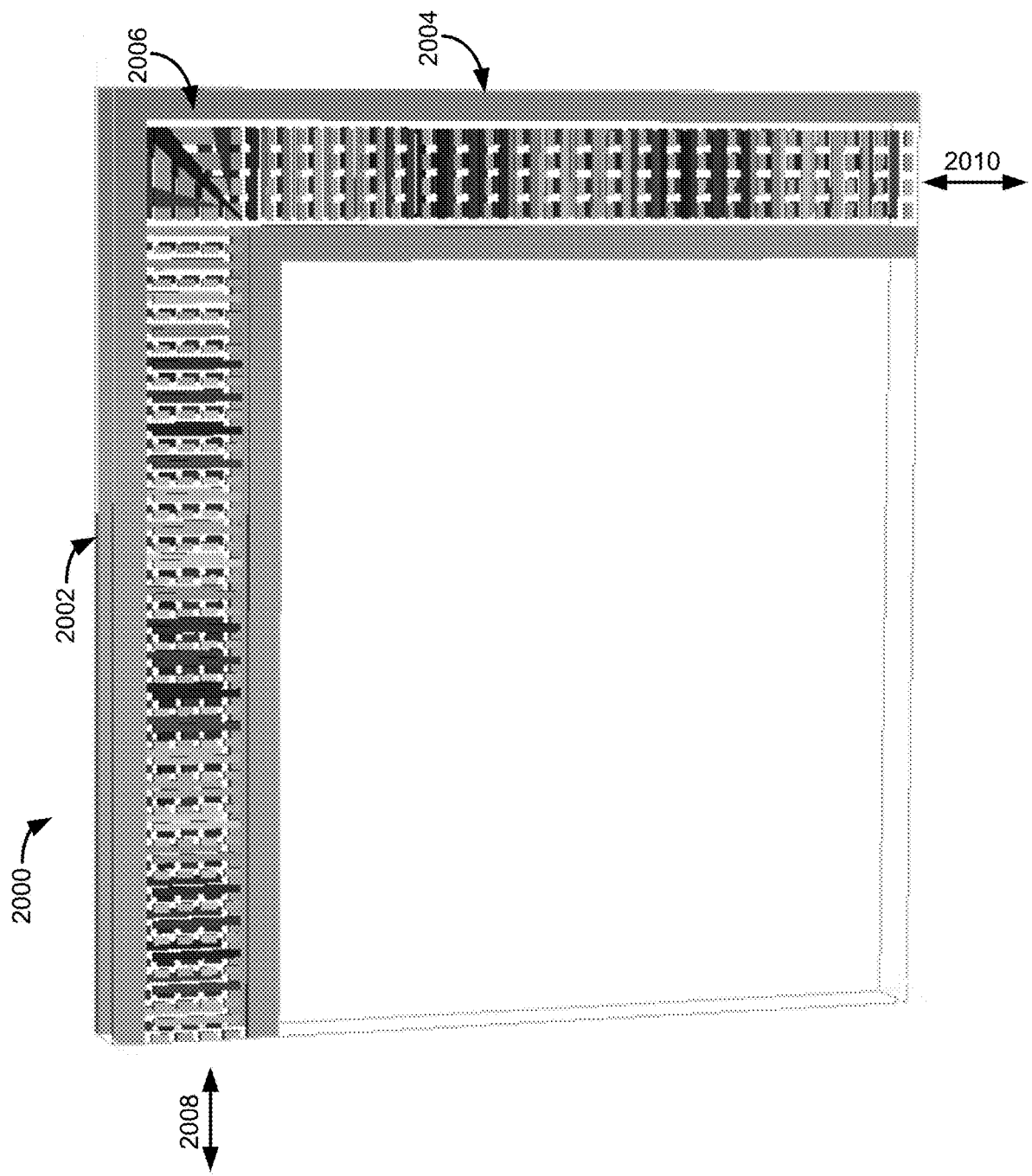
FIGS. 20-22 show various views of another exemplary embodiment of the disclosed ion manipulation devices.

FIG. 20 shows an exemplary ion manipulation device 2000. The device 2000 comprises two parallel surfaces separated by a short distance such that ions can be guided between the two surfaces. The device 2000 comprises a first portion 2002 and a second portion 2004 arranged at a 90° angle with respect to each other and connected by a corner section 2006. FIG. 2I shows a close-up view of the corner section 2006. The first and second portions 2002, 2004 of FIG. 20 are each constructed similar to the device 1800 of FIGS. 18A-18C. The first and second portions 2002, 2004 have an upper and lower surface each comprising outer guard electrodes and central confinement electrodes. The first portion 2002 has a longitudinal axis 2008 and the second portion 2004 has a longitudinal axis 2010. Voltages can be applied to the guard electrodes to confine ions to the center of the device in a similar manner as discussed above in connection with the guard electrodes 1805, 1806, 1807, 1808 of FIG. 18B. The confinement electrodes consist of alternating segmented electrode rows and unsegmented electrodes. Voltages can be applied to the electrode rows in a similar manner as discussed above in connection with the electrode rows of FIG. 18A to create a rotating traveling wave that can confine ions between the two parallel surfaces. Voltages can be applied to the unsegmented electrodes of the first and second portions 2002, 2004 to move ions through the device 2000 along longitudinal axes 2008, 2010 respectively in a similar manner as discussed above in connection with FIGS. 18A-18C. In the illustrated example, a transient DC voltage is applied to the unsegmented electrodes to create a traveling wave that guides ion through the device 2000. In other examples, a DC voltage gradient is applied to the unsegmented electrodes to guide ions through the device.

The corner portion 2006 is positioned at the junction between the first and second portions 2002, 2004 of the device 2000. The corner portion can guide ions such that they turn the corner from the first portion 2002 to the second portion 2004 or vice versa. In the illustrated example, the upper surface of the corner portion 2006 includes segmented electrodes 2010, 2012, 2014, 2016 and unsegmented electrodes 2018, 2020, 2022. The lower portion contains similar corresponding electrodes positioned directly across. The segmented electrodes 2010, 2012, 2014, 2016 can confine ions between the upper and lower surface of the corner portion 2006, similar to the segmented electrodes of the first and second portions 2002, 2004. The unsegmented electrodes 2018, 2020, 2022 of the corner portion 2006 can guide ions to turn around the corner.

Figure 21:
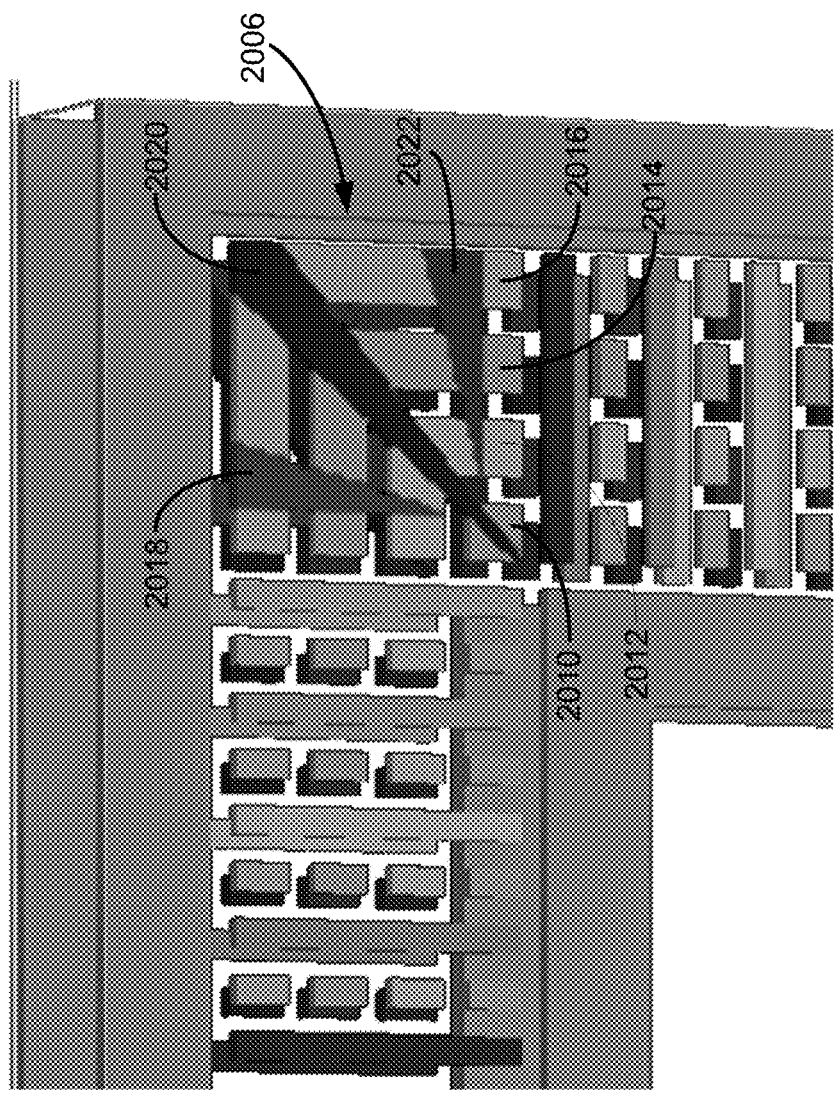

In the illustrated example of FIGS. 20-21, electrode 2010 is a rectangular shaped electrode positioned in the lower left corner of the corner portion 2006 and the electrodes 2012, 2014, 2016 are L-shaped electrodes positioned such that one portion of their L-shape extends parallel to the longitudinal axis 2008 and one portion of their L-shape extends parallel to the longitudinal axis 2010. A rotating voltage profile can be applied to the segmented electrodes of the corner portion 2006 to create a rotating traveling wave that confines ion between the parallel surfaces of the corner portion. For example, a voltage can be applied to electrode 2010 during a first time interval, then to electrode 2012 during a second time interval, then in subsequent time intervals a voltage can be subsequently applied to electrode 2014, then to electrode 2016, then to the electrode across from electrode 2016 on the lower surface, then to the electrode across from electrode 2014, then to the electrode across from 2012, then to the electrode across from electrode 2010. In other examples, a voltage can be applied to more than one segmented electrode at a time so long as the electrodes to which a voltage is applied rotates over time.

One or more voltages can be applied to the unsegmented electrodes 2018, 2020, 2022 of the corner portion 2006 to guide ions around the corner. In the illustrated example, there are three unsegmented electrodes in the corner portion 2006. In other examples, there can be more or less than three unsegmented electrodes in the corner portion 2006. In the illustrated example, the unsegmented electrodes 2018, 2020, 2022 are angled with respect to the unsegmented electrodes of the first portion 2002 and the second portion 2004. In the illustrated example, the electrode 2018 is slightly angled with respect to the unsegmented electrodes of the first portion 2002, the electrode 2022 is slightly angled with respect to the unsegmented electrodes of the second portion 2004, and the electrode 2020 is positioned at a 45° angle with respect to the unsegmented electrodes of the first portion and the unsegmented electrodes of the second portion. As such, as ions enter the corner portion 2006 from either the first portion 2002 or the second portion 2004, the gradually increasing angle of the unsegmented electrodes 2018, 2020, 2022 causes those ions to bend around the corner. In the illustrated example, a transient DC voltage is applied to the electrodes 2018, 2020, 2022 in a similar manner as with the unsegmented electrodes of the first or second portions 2002, 2004 of the device 2000 to create a traveling wave that guides ions around the corner. In other examples where a DC voltage gradient is applied to the unsegmented electrodes of the first and second portions 2002, 2004, a similar DC voltage gradient is applied to the electrodes 2018, 2020, 2022 of the corner portion 2006.

Figure 22:
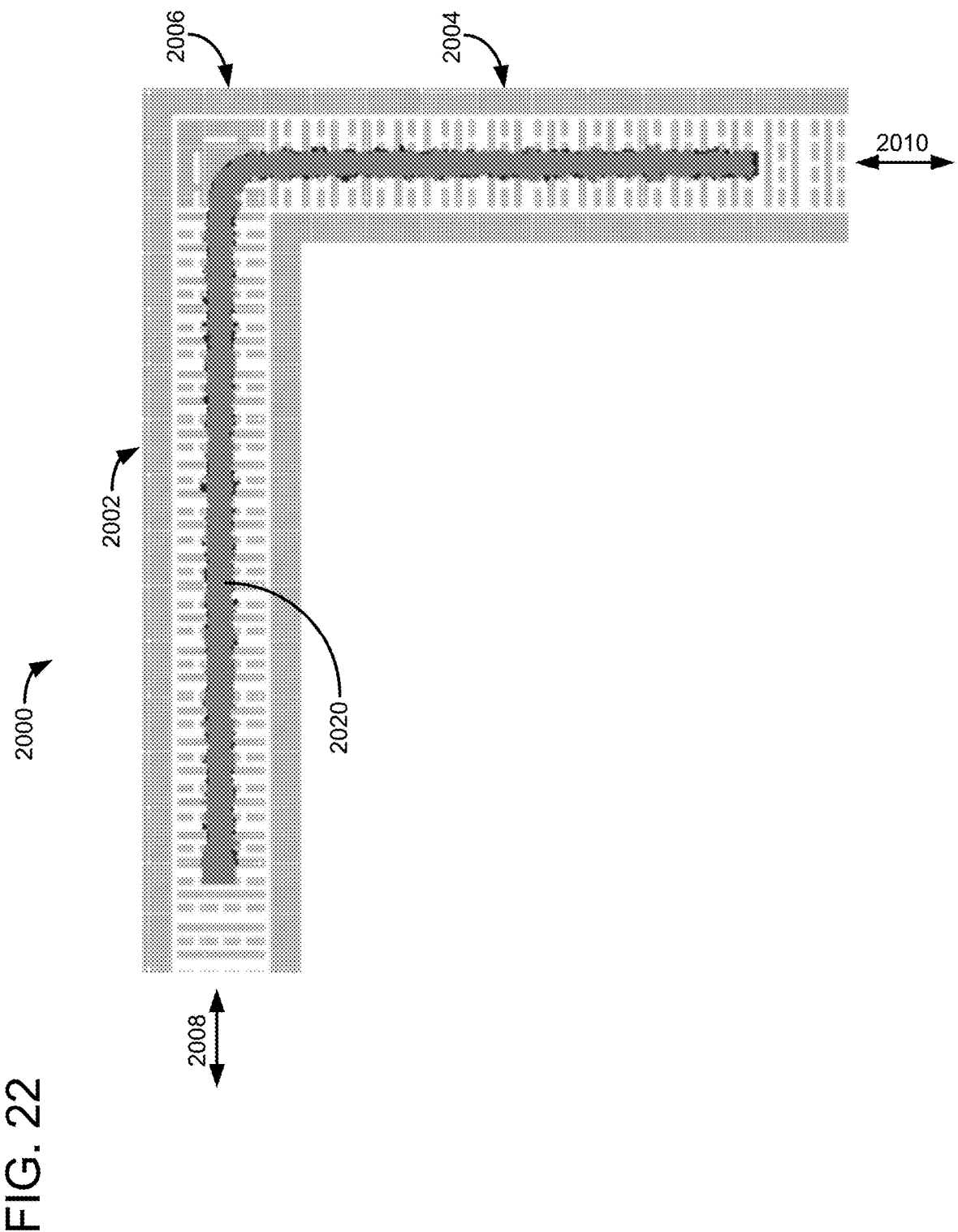
Figure 23:
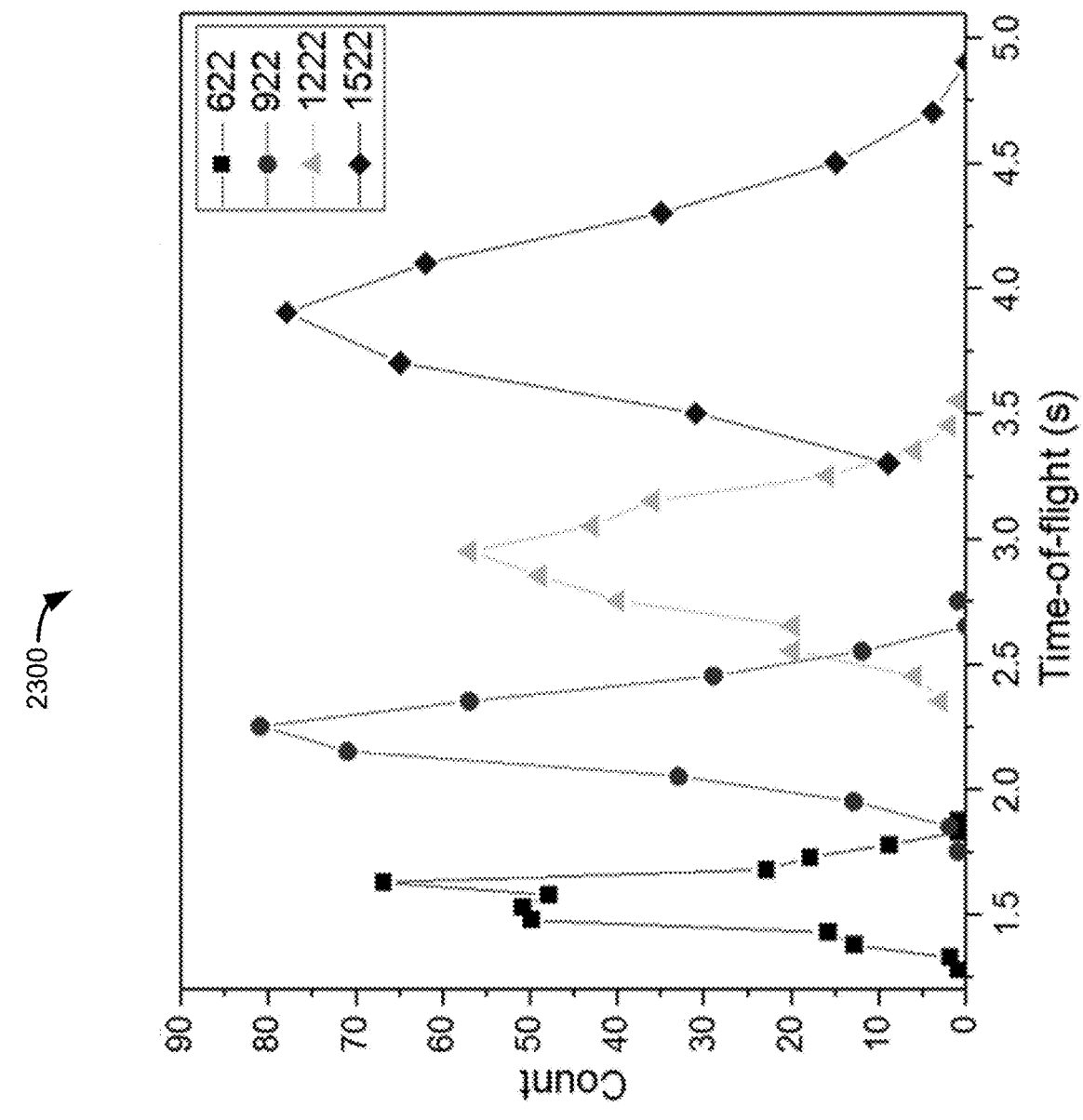
FIG. 23 shows a plot of simulation results of ions traveling through the ion manipulation device of FIGS. 20-22.

FIG. 22 shows a simulation of an ion cloud 2020 moving through the device 2000 and around the corner of the corner piece 2006. FIG. 23 shows a plot 2300 of simulation results of ions of different mass moving through the device 2000.

Figure 24:
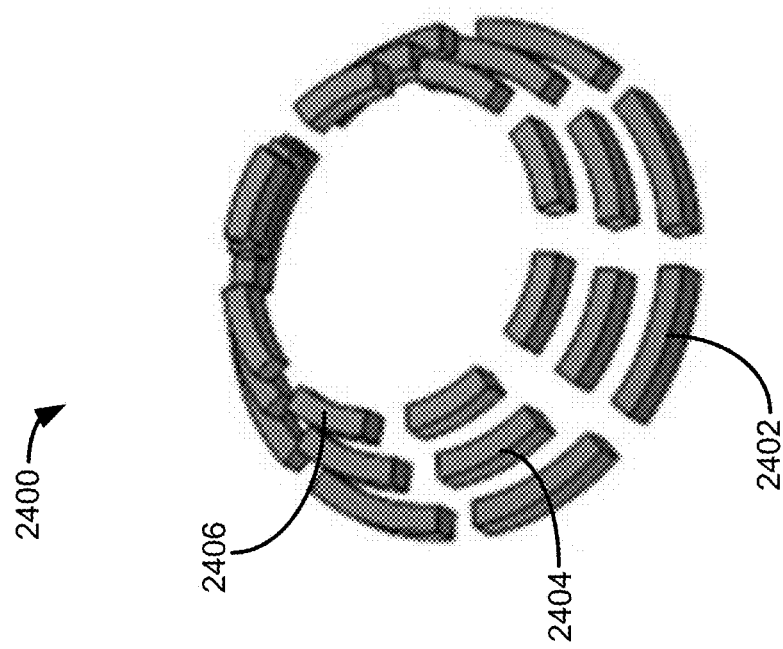
FIG. 24 shows a perspective view of another exemplary embodiment of the disclosed ion manipulation devices.

FIG. 24 shows an exemplary ion manipulation device 2400. The device 2400 of FIG. 24 is constructed in a similar manner to the device 300 of FIG. 3 except that the electrode rings of the device 2400 have a narrower inner diameter moving along the central axis of the device. In the illustrated example, the device 2400 has three electrode rings 2402, 2404, 2406. In other examples, the device can comprise additional electrode rings. Each electrode rings comprises a plurality of segmented electrodes arranged in a circular pattern and each electrode ring has a smaller diameter than the adjacent electrode ring when moving axially along the device. Voltages can be applied to the electrodes to create a circular traveling wave around each electrode ring to confine ions and an axial traveling wave or axial DC voltage gradient to move ions through the device. The funnel shape of the device 2400 can funnel ions from a wider area into a narrower area.

Other embodiments are within the scope and spirit of the disclosed subject matter. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, a data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The devices, methods and apparatus described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

We claim:

1. An ion manipulation device comprising:
   a plurality of electrode rings arranged longitudinally adjacent to each other and defining a central axis therethrough;
   at least one electrode ring comprising a plurality of electrodes arranged in a first planar pattern;
   wherein the plurality of electrodes are configured to periodically receive a voltage to generate a circular traveling wave that rotates around the electrodes of the at least one electrode ring to confine ions within an interior of the apparatus.

2. The device of claim 1, wherein the first planar pattern has rotational symmetry.

3. The device of claim 1, wherein the first planar pattern defines an enclosed volume.

4. The device of claim 1, wherein the first planar pattern is a circular arrangement of electrodes.

5. The device of claim 1, wherein the first planar pattern is a rectangular arrangement of electrodes.

6. The device of claim 1, wherein there is a gap between at least one pair of axially adjacent electrode rings.

7. The device of claim 6, wherein the gap is sized such that the electrodes of one electrode ring of the at least one pair of axially adjacent electrode rings are electrically isolated from the electrodes of the other of the electrode rings of the at least one pair of axially adjacent electrode rings.

8. The device of claim 1, wherein there is a dielectric material positioned between at least one pair of axially adjacent electrode rings.

9. The device of claim 1, wherein the circular traveling wave on at least one electrode ring is out of phase with the circular traveling wave on an adjacent electrode ring.

10. The device of claim 1, wherein there is a gap between two radially adjacent electrodes of at least one electrode ring.

11. The device of claim 1, wherein at least two of the electrode rings are configured to receive a superimposed DC voltage to create a DC voltage gradient along a length of the apparatus to guide ions along the central axis.

12. The device of claim 1, wherein at least two of the electrode rings are configured to receive a superimposed transient DC voltage to create an axial traveling wave to guide ions along the central axis.

13. The device of claim 1, further comprising a second plurality of segmented electrodes radially interleaved between the electrodes of at least one electrode ring.

14. The device of claim 13, wherein the second plurality of segmented electrodes are configured to receive a DC voltage to create a DC voltage gradient along a length of the apparatus to guide ions along the central axis.

15. The device of claim 13, wherein the second plurality of segmented electrodes are configured to receive a superimposed transient DC voltage to create an axial traveling wave to guide ions along the central axis.

16. The device of claim 1, wherein the electrode rings form a substantially T-shaped or Y-shaped configuration, allowing ions to be switched at a junction of the T-shaped or Y-shaped configuration.

17. The device of claim 1, further comprising a plurality of unsegmented electrodes axially interleaved between at least two adjacent electrode rings.

18. The device of claim 17, wherein the unsegmented electrodes are configured to receive a DC voltage to create an axial electric field gradient along a direction of the unsegmented electrodes to guide the ions along a central axis.

19. The device of claim 17, wherein the unsegmented electrodes are configured to receive a transient DC voltage to create an axial traveling wave to guide ions along the central axis.

20. A method of manipulating ions comprising:
   injecting ions within an interior of an apparatus comprising a plurality of electrode rings arranged longitudinally adjacent to each other and defining a central axis therethrough, wherein at least one electrode ring comprises a plurality of electrodes arranged in a first planar pattern; and
   applying a periodic voltage to at least two electrodes of at least one electrode ring to generate a circular traveling wave that rotates around the electrodes of each electrode ring to confine ions within the interior of the apparatus.

21. The method of claim 20, further comprising:
applying a superimposed DC voltage to at least two electrode rings to create a DC voltage gradient along a length of the apparatus to guide ions along the central axis.

22. The method of claim 20, further comprising:
applying a superimposed transient DC voltage to the electrode rings to create an axial traveling wave to guide ions along the central axis.

* * * * *